United States Patent
Aldrich et al.

(10) Patent No.: US 11,820,835 B2
(45) Date of Patent: Nov. 21, 2023

(54) CYCLIC TETRAPEPTIDE ANALOGS

(71) Applicants: University of Kansas, Lawrence, KS (US); UNIVERSITY OF FLORIDA RESEARCH FOUNDATION, INC., Gainesville, FL (US)

(72) Inventors: Jane Aldrich, Gainesville, FL (US); Sanjeewa Senadheera, Lancaster, PA (US); Jay McLaughlin, Gainesville, FL (US)

(73) Assignees: UNIVERSITY OF KANSAS, Lawrence, KS (US); UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 0 days.

(21) Appl. No.: 16/982,638

(22) PCT Filed: Mar. 22, 2019

(86) PCT No.: PCT/US2019/023698
§ 371 (c)(1),
(2) Date: Sep. 21, 2020

(87) PCT Pub. No.: WO2019/183556
PCT Pub. Date: Sep. 26, 2019

(65) Prior Publication Data
US 2021/0024576 A1    Jan. 28, 2021

Related U.S. Application Data

(60) Provisional application No. 62/647,287, filed on Mar. 23, 2018.

(51) Int. Cl.
C07K 5/12         (2006.01)
A61K 9/00        (2006.01)
A61K 38/00       (2006.01)

(52) U.S. Cl.
CPC ............ *C07K 5/126* (2013.01); *A61K 9/0053* (2013.01); *A61K 38/00* (2013.01)

(58) Field of Classification Search
CPC ....... A61K 38/00; A61K 9/0053; A61P 25/30; C07K 5/126
See application file for complete search history.

(56) References Cited

U.S. PATENT DOCUMENTS 5,885,959 A      3/1999 Hirai et al.
8,906,844 B2 *  12/2014 Mezo ................... C07K 7/08
                                                           514/1.1
(Continued)

FOREIGN PATENT DOCUMENTS

WO   WO-2016007956 A2 *  1/2016 ............... C07K 5/12
WO   WO-2016/061531 A1   4/2016

OTHER PUBLICATIONS

Livingstone et al., Cabios, vol. 9(6):745-756 (1993) (Year: 1993).*
(Continued)

*Primary Examiner* — Randall L Beane
(74) *Attorney, Agent, or Firm* — Foley & Lardner LLP

(57) ABSTRACT

The present technology provides compounds of Formula I (or pharmaceutically acceptable salts and/or solvates thereof) that are useful in treating a CNS-related disorder such as schizophrenia, schizoaffective disorder, migraine, depression, pain, drug addiction, drug use, and/or drug (Continued)

seeking behavior. Also provided are compositions, medicaments, and methods including such compounds.

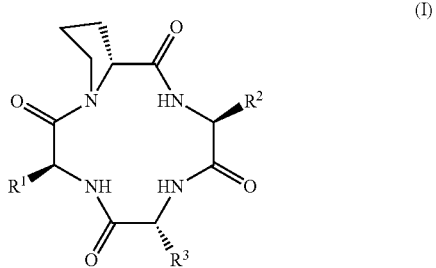

(I)

17 Claims, 26 Drawing Sheets

(56) References Cited

U.S. PATENT DOCUMENTS

| | | | |
|---|---|---|---|
| 10,259,843 | B2 | 4/2019 | Aldrich et al. |
| 2002/0120099 | A1 | 8/2002 | Nishino et al. |
| 2011/0190212 | A1* | 8/2011 | Aldrich ............... A61K 31/409 |
| | | | 514/17.6 |
| 2011/0195915 | A1 | 8/2011 | Graham et al. |
| 2015/0202173 | A1 | 7/2015 | Gari et al. |
| 2017/0190738 | A1 | 7/2017 | Aldrich et al. |
| 2017/0369531 | A1 | 12/2017 | Zadina et al. |

OTHER PUBLICATIONS

Choi et al., Statistically Speaking It's just a standard deviation, Anaethesia, vol. 71:969-971 (2016) (Year: 2016).*
Dolle et al., Nascent structure-activity relationship study of a diastereomeric series of kappa opioid receptor antagonists derived from CJ-15,208, Bioorganic & Medicinal Chemistry Letters, vol. 19:3647-3650 (May 3, 2009) (Year: 2009).*
Aldrich et al., "Alanine analogues of [D-Trp ]CJ-15,208: novel opioid activity profiles and prevention of drug- and stress-induced reinstatement of cocaine-seeking behaviour", British Journal of Pharmacology, 2014, vol. 171, pp. 3212-3222.
Aldrich et al., "Unexpected Opioid Activity Profiles of Analogues of the Novel Peptide Kappa Opioid Receptor Ligand CJ-15,208", ChemMedChem, 2011, vol. 6, pp. 1739-1745.
Communication Pursuant to Article 94(3) mailed in EP 18741702.7 dated Aug. 2, 2021 (4 pages).
Communication pursuant to Rules 70(2) and 70a(2) EPC in EP Patent Application No. 18741702.7 dated Oct. 20, 2020 (1 page).
De Marco et al., "Versatile Picklocks To Access All Opioid Receptors: Tuning the Selectivity and Functional Profile of the Cyclotetrapeptide c[Phe-D-Pro-Phe-Trp] (CJ-15,208)", Journal of Medicinal Chemistry, 2016, vol. 59, pp. 9255-9261.
Deveza, et al., "Microfluidic Synthesis of Biodegradable Polyethylene-Glycol Microspheres for Controlled Delivery of Proteins and DNA Nanoparticles," ACS Biomater. Sci. Eng., 2015, vol. 1, pp. 157-165.
Extended European Search Report in EP Patent Application No. 18741702.7 dated Sep. 30, 2020 (8 pages).
Extended European Search Report on EP Patent Application No. 19771690.5 dated Nov. 19, 2021, (11 pages).
Fukuda, et al., "Functional coupling of the delta-, mu-, and kappa-opioid receptors to mitogen-activated protein kinase and arachidonate release in Chinese hamster ovary cells," J. Neurochem., 1996, vol. 67, No. 3 (abstract only) (2 pages).
Gentilucci et al., Molecular Docking of Opiates and Opioid Peptides, a Tool for the Design of Selective Agonists and Antagonists, and for the Investigation of Atypical Ligand-Receptor Interactions, Current Medicinal Chemistry, Apr. 1, 2012, vol. 19, No. 11, pp. 1587-1601.
International Preliminary Reporton Patentability in International Patent Application No. PCT/US2018/014595 dated Jul. 23, 2019 (9 pages).
International Search Report and Written Opinion in International Patent Application No. PCT/US2018/014595 dated May 15, 2018 (12 pages).
Maneckjee et al., "Binding of Opioids to Human MCF-7 Breast Cancer Cells and Their Effects on Growth", Cancer Research, Apr. 15, 1990, vol. 50, No. 8, pp. 2234-2238.
Mukhopadhyay et al., "Macrocyclic Peptides Decrease c-Myc Protein Levels and Reduce Prostate Cancer Cell Growth", Cancer Biology & Therapy, Aug. 3, 2017, vol. 18, No. 8, pp. 571-583.
Non-Final Office Action mailed in U.S. Appl. No. 16/479,063 dated Apr. 17, 2020 (17 pages).
Restriction Requirement mailed in U.S. Appl. No. 16/479,063 dated Feb. 7, 2020 (9 pages).
Restriction Requirement mailed in U.S. Appl. No. 17/072,409 dated Oct. 7, 2021 (6 pages).
Ross, et al., "Synthesis of CJ-15,208, a novel k-opioid receptor antagonist", Tetrahedron Letters, Elsevier Ltd, Amsterdam, NL, Sep. 22, 2010, vol. 51, No. 38, pp. 5020-5023.
Singelton, et al., "The Mu Opioid Receptor: A New Target for Cancer Therapy?", Cancer, Aug. 15, 2015, vol. 121, No. 16, pp. 2681-2688.
International Search Report and Written Opinion in International Patent Application No. PCT/US2019/023698 dated Jun. 7, 2019 (16 pages).
Aldrich et al., "The Macrocyclic Peptide Natural Product CJ-15,208 Is Orally Active and Prevents Reinstatement of Extinguished Cocaine-Seeking Behavior", J Nat Prod., vol. 76, 2013, p. 433-438.
Eans et al., "The macrocyclic tetrapeptide [D-Trp]CJ-15,208 produces short-acting κ opioid receptor antagonism in the CNS after oral administration", Br J Pharmacol., vol. 169, 2013, pp. 426-436.
First Examination Report on IN 202017044153 dated Mar. 31, 2022 (6 pages).
Tallarida et al., "Manual of Pharmacologic Calculations with Computer Programs", 2012 (304 pages).

* cited by examiner

CYCLIC TETRAPEPTIDE ANALOGS

CROSS-REFERENCE TO RELATED APPLICATIONS

This application is a U.S. National Phase Application under 35 U.S.C. § 371 of International Application No. PCT/US2019/023698, filed Mar. 22, 2019, which claims the benefit of and priority to U.S. Provisional Application No. 62/647,287, filed Mar. 23, 2018, the entireties of each of which are hereby incorporated by reference for any and all purposes.

U.S. GOVERNMENT RIGHTS

This invention was made with government support under grant number DA032928 awarded by the National Institutes of Health and grant numbers W81XWH-15-1-0452 and W81XWH-15-1-0464 awarded by the Department of Defense. The government has certain rights in the invention.

FIELD

The present technology directed to cyclic tetrapeptide compounds that are useful in treating a CNS-related disorder such as schizophrenia, schizoaffective disorder, migraine, depression, pain, drug addiction, drug use, and/or drug seeking behavior, as well as compositions, medicaments, and methods including such cyclic tetrapeptide compounds.

SUMMARY

In an aspect, a compound of Formula I is provided

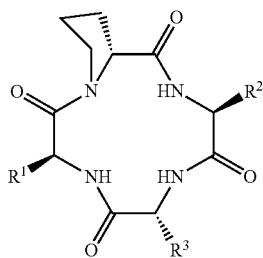

(I)

or a pharmaceutically acceptable salt and/or solvate thereof, wherein $R^1$ and $R^2$ are each independently

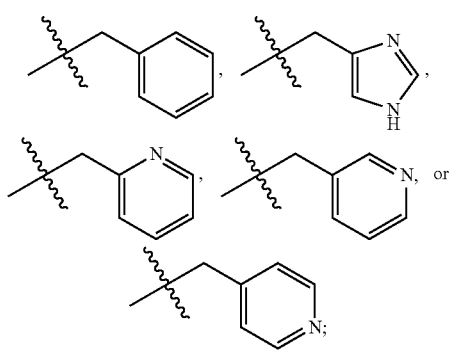

and $R^3$ is

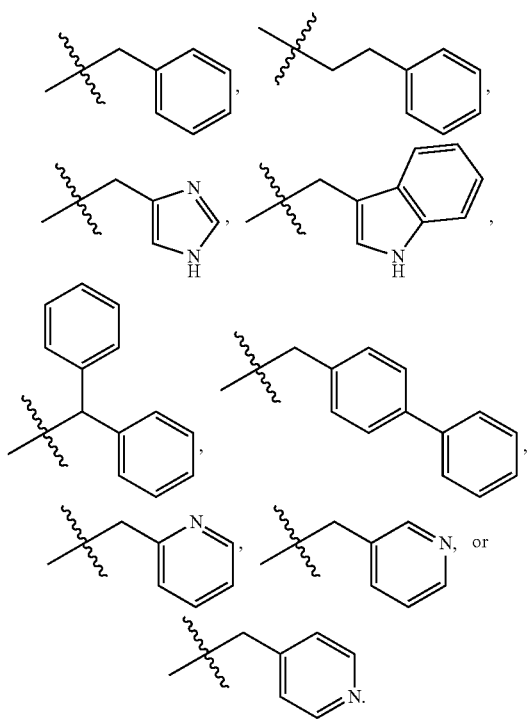

In a related aspect, a composition is provided that includes a compound of any embodiment disclosed herein of Formula I as well as a pharmaceutically acceptable carrier.

In a further related aspect, a pharmaceutical composition is provided that includes an effective amount of a compound of any embodiment disclosed herein of Formula I and includes a pharmaceutically acceptable carrier, where the effective amount is effective for treating and/or inhibiting a CNS-related disorder (such as pain, schizophrenia, schizoaffective disorder, migraine, depression, drug addiction, drug use, and/or drug seeking behavior) in a subject.

In an aspect, a method is provided where the method includes administering an effective amount of a compound of any embodiment disclosed herein of Formula I (or administering a pharmaceutical composition of any embodiment disclosed herein) to a subject suffering from a CNS-related disorder (such as pain, schizophrenia, schizoaffective disorder, migraine, depression, drug addiction, drug use, and/or drug seeking behavior).

In an aspect, a method is provided where the method includes administering an effective amount of a compound of any embodiment disclosed herein of Formula I (or administering a pharmaceutical composition of any embodiment disclosed herein) to a subject suffering from pain, provided that the compound is not JVA-3627 or JVA-3629.

In an aspect, a method is provided where the method includes contacting a kappa opioid receptor with a compound of any embodiment disclosed herein of Formula I wherein the contacting agonizes and/or antagonizes the kappa opioid receptor.

BRIEF DESCRIPTION OF THE DRAWINGS

FIG. 1A provides antinociception (left side) and KOR antagonism (right side) of JVA-3620 after central (i.c.v.) administration, FIG. 1B provides antinociception (left side) and KOR antagonism (right side) of JVA-3620 after oral (p.o.) administration, FIG. 1C provides the results of orally administered JVA-3620 antagonism of centrally (i.c.v.) administered KOR agonist U50,488, FIG. 1D illustrates that the opioid antagonism is selective for KOR, and FIG. 1E illustrates that orally administered JVA-3620 can prevent stress-induced relapse to cocaine-seeking behavior.

FIG. 2A provides antinociception (left side) and KOR antagonism (right side) of JVA-3628 after central (i.c.v.) administration, FIG. 2B provides antinociception (left side) and KOR antagonism (right side) of JVA-3628 after oral (p.o.) administration, FIG. 2C provides the results of orally administered JVA-3628 antagonism of centrally (i.c.v.) administered KOR agonist U50,488, FIG. 2D illustrates that the opioid antagonism is selective for KOR, and FIG. 2E illustrates that orally administered JVA-3628 can prevent stress-induced relapse to cocaine-seeking behavior.

FIG. 6A illustrates that orally administered (10 or 30 mg/kg p.o.) JVA-3620 does not produce hyperlocomotion like morphine, but instead can significantly decrease locomotion during the first hour. FIG. 6B illustrates that JVA-3620 decreases respiration during the first hour, but whether or not such decreased respiration is related to the decreased locomotion is unknown from this data.

FIG. 7A illustrates that orally administered (10 or 30 mg/kg p.o.) JVA-3628 does not produce hyperlocomotion like morphine, but instead can significantly decrease locomotion during the first hour. FIG. 7B illustrates that JVA-3628 decreases respiration during the first hour, but whether or not such decreased respiration is related to the decreased locomotion is unknown from this data.

DETAILED DESCRIPTION

Figure 1A:
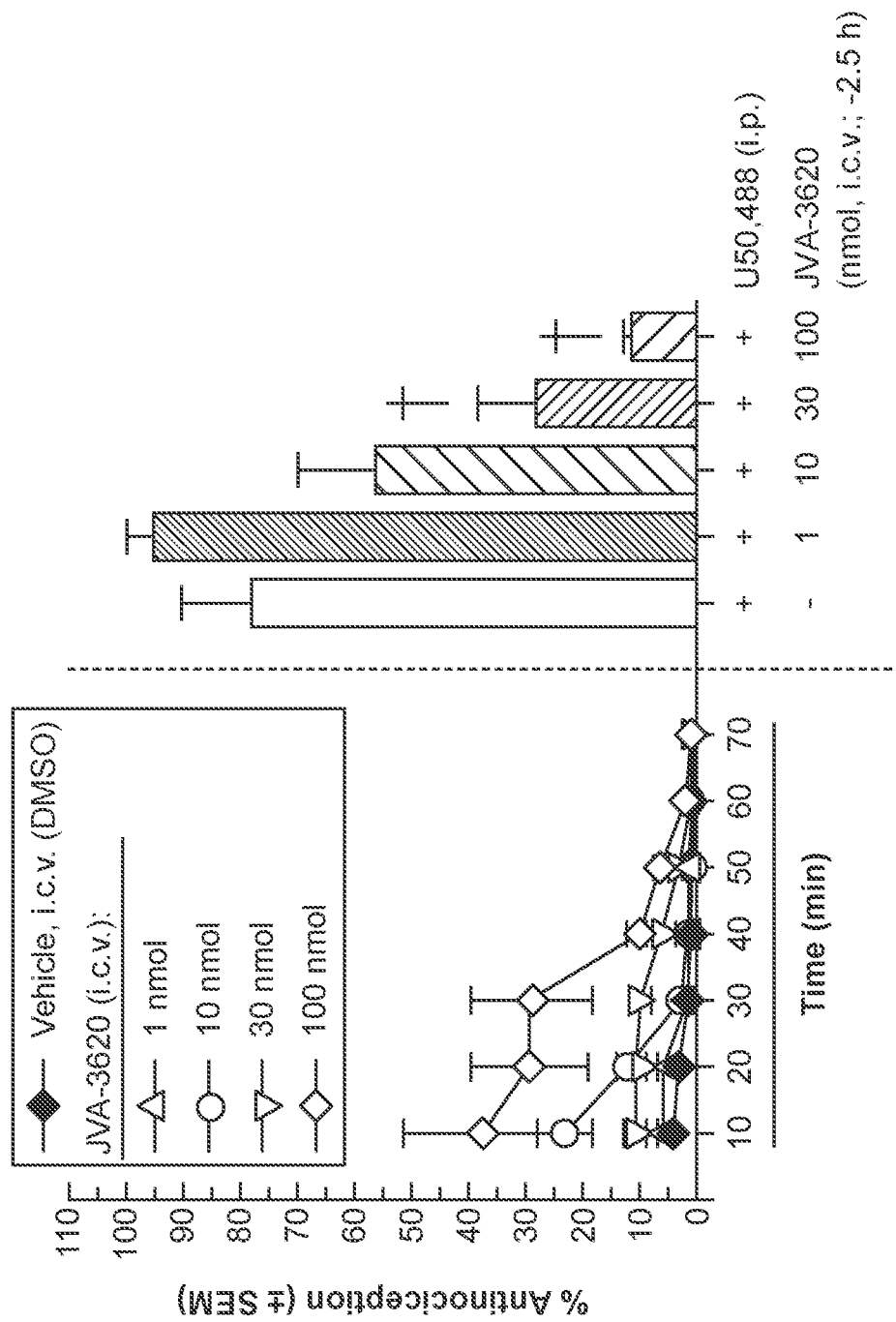
FIGS. 1A-E provides in vivo data for JVA-3260 (a compound of the present technology) in mice.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would mean "9 wt. % to 11 wt. %."

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $ca^{2+}$, $mg^{2+}$, $zn^{2+}$) ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

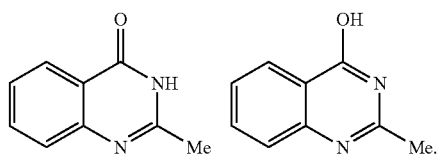

As another example, guanidines may exhibit the following isomeric forms in protic organic solution, also referred to as tautomers of each other:

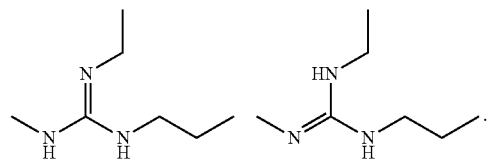

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents, and published patent specifications are referenced by an identifying citation. Also within this disclosure are Arabic numerals referring to referenced citations, the full bibliographic details of which are provided immediately preceding the claims. The disclosures of these publications, patents, and published patent specifications are hereby incorporated by reference into the present disclosure to more fully describe the state of the art to which this invention pertains.

The Present Technology

Major depression is estimated to affect approximately 15 million American adults (6.7% of the adult population; Anxiety and Depression Association of America). Kappa opioid receptor (KOR) antagonists are useful in treatment of such conditions, as well as for treatment of addictive substances, including nicotine and opioids.

Some selective small molecule kappa opioid receptor (KOR) antagonists such as JDTic (which was evaluated in a Phase 1 clinical trial) have exceptionally long duration of activity after a single dose (weeks in some species) which may raise safety concerns for their use. Other KOR antagonists are being developed as potential therapeutic agents. LY2456302 (CERC 501) is a KOR antagonist discovered by Eli Lily that is under development for major depressive disorders and substance abuse disorders (nicotine, alcohol and/or cocaine). The clinically used opioid mu opioid receptor partial agonist/KOR antagonist buprenorphine has been combined with the mu opioid receptor antagonist samidorphan to give ALK-5461 that functions as a KOR antagonist; it has undergone several Phase III clinical trials for the treatment of depression and was recently submitted under a new drug application to the Food and Drug Administration.

[D-Trp]CJ-15,208 (illustrated below) exhibits a more typical duration of action than JDTic (<18 hours; Ross et al., 2012; Eans et al., 2013) so that prolonged activity is not an issue.

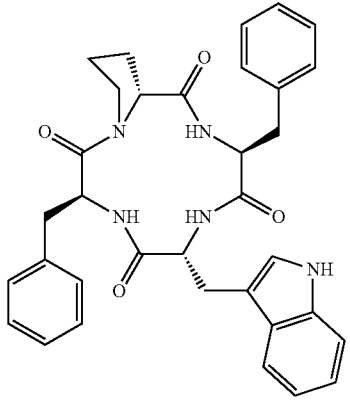

[D-Trp]CJ-15,208

There is further need for compounds (particularly peptide-based compounds) with KOR activity and improved pharmacokinetic properties. Peptides often are more specific and have less off-target activities (and therefore potentially fewer side effects) than small molecule drugs.

Thus, in an aspect, a compound of Formula I is provided

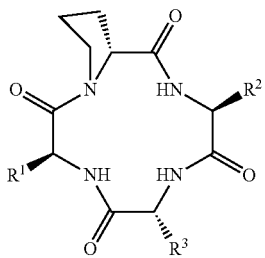
(I)

or a pharmaceutically acceptable salt and/or solvate thereof, wherein $R^1$ and $R^2$ are each independently

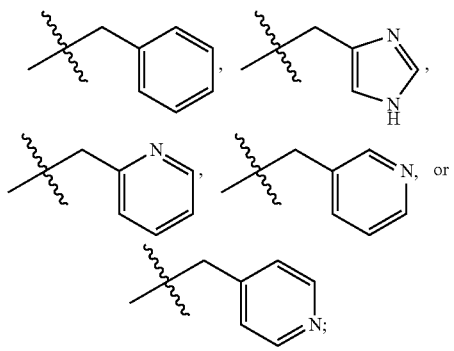

and $R^3$ is

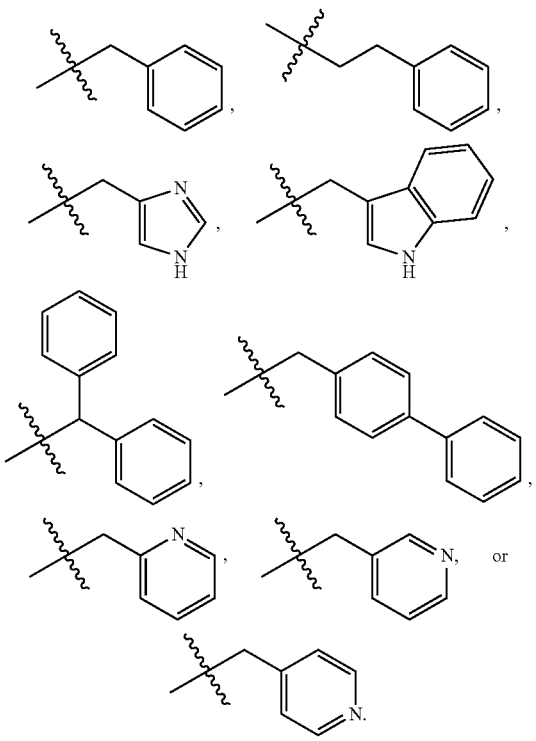

The macrocyclic tetrapeptide compounds of the present technology are a completely different structural class from typical opioid small molecule ligands and are structurally very different from endogenous opioid peptides. Various embodiments contain novel amino acid derivatives (e.g., pyridylalanine isomers). Moreover, heteroatom-containing side chains typically have lower lipophilicity than [D-Trp]CJ-15,208 (cLog P=5.0) providing improved physiochemical properties of the compounds.

In any embodiment herein, the compound of Formula I may be of Formula II

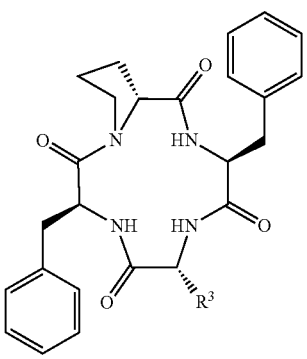
(II)

or a pharmaceutically acceptable salt and/or solvate thereof.

In any embodiment herein, the compound of Formula I may be of Formula III

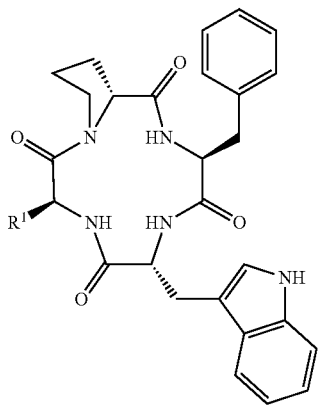

(III)

or a pharmaceutically acceptable salt and/or solvate thereof.

In any embodiment herein, the compound of Formula I may be of Formula IV

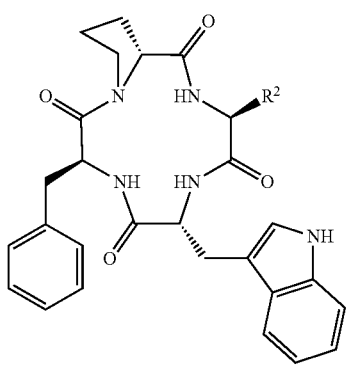

(IV)

or a pharmaceutically acceptable salt and/or solvate thereof.

The present technology provides compositions (e.g., pharmaceutical compositions) and medicaments comprising any of one of the embodiments of the compounds of Formulas I-IV (or a pharmaceutically acceptable salt thereof) disclosed herein and a pharmaceutically acceptable carrier or one or more excipients or fillers. The compositions may be used in the methods and treatments described herein. The pharmaceutical composition may include an effective amount of any of one of the embodiments of the compounds of the present technology disclosed herein.

In an aspect, the present technology provides a method that includes administering an effective amount of a compound of the present technology (or administering a pharmaceutical composition or medicament of the present technology) to a subject suffering from a CNS-related disorder. The CNS-related disorder may be a substance abuse disorder and/or withdrawal syndrome (such as drug seeking behavior, drug use, and/or a drug addiction to, e.g., opiates, opioids, cocaine, and/or alcohol), a mood disorder (such as depression, dysthymic disorder, and/or bipolar disorder), an anxiety disorder and/or compulsive disorder (such as obsessive-compulsive disorder (OCD), social phobia, generalized anxiety disorder (GAD), and/or social anxiety disorder), stress, post-traumatic stress disorder (PTSD), a schizophrenia spectrum disorder (such as schizophrenia and/or schizoaffective disorder), pain (such as migraine, neuropathic pain, an injury related pain syndrome, acute pain, and/or chronic pain), a personality disorder (such as anti-social personality disorder and/or obsessive compulsive personality disorder), an autism spectrum disorder (ASD) (such as autism and/or a monogenetic cause of autism such as synaptophathy's, e.g., Rett syndrome, Fragile X syndrome, Angelman syndrome), an eating disorders; sleep disorders (including insonmia); a disorder of memory and/or cognition (such as an attention disorder (e.g., attention deficit hyperactivity disorder (ADHD)), dementia (such as Alzheimer's type dementia, Lewis body type dementia, and/or vascular type dementia), head shock and traumatic brain injury (TBI), a vascular disease (such as stroke, ischemia, and/or vascular malformations), and a cognitive disorder (such as Alzheimer's disease). In any embodiment disclosed herein, the effective amount may be the amount that is effective to treat the CNS-related disorder. In any embodiment herein, the subject may be suffering from pain, schizophrenia, schizoaffective disorder, migraine, depression, drug addiction, drug use, and/or drug seeking behavior. In any embodiment disclosed herein, the effective amount may be the amount that is effective to treat pain, schizophrenia, schizoaffective disorder, migraine, depression, drug addiction, drug use, and/or drug seeking behavior in the subject.

In an aspect, the present technology provides a method that includes administering an effective amount of a compound of the present technology (or administering a pharmaceutical composition or medicament of the present technology) to a subject suffering from pain, provided that the compound is not JVA-3627 or JVA-3629 (and/or that the pharmaceutical composition does not include JVA-3627, JVA-3629, or both JVA-3627 and JVA-3629, and/or that the medicament does not include JVA-3627, JVA-3629, or both JVA-3627 and JVA-3629). In any embodiment disclosed herein, the effective amount may be the amount that is effective to treat pain in the subject.

In a further aspect, the present technology provides a method that includes contacting a kappa opioid receptor with a compound of the present technology wherein the contacting agonizes and/or antagonizes the kappa opioid receptor. The contacting may occur in vitro or in vivo. In any embodiment disclosed herein of the method, the method may further include contacting a mu opioid receptor, wherein the contacting does not antagonize the mu opioid receptor (such as by use of an amount effective to antagonize the kappa opioid receptor but not the mu opioid receptor). In any embodiment disclosed herein of the method, the method may further include contacting a delta opioid receptor, wherein the contacting does not antagonize the delta opioid receptor (such as by use of an amount effective to antagonize the kappa opioid receptor but not the delta opioid receptor).

In any of the above embodiments, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of depression, pain, drug addiction, drug use, and/or drug seeking behavior. The effective amount may be from about 0.01 µg to about 500 mg of the compound per gram of the composition, and preferably from about 0.1 µg to about 100 mg of the compound per gram of the composition. As used herein, a "subject" or "patient" is a mammal, such as a cat, dog, rodent or primate. Typically the subject is a human, and, preferably, a human suffering from or suspected of suffering from depression, pain, drug addiction, drug use, and/or drug seeking behavior. The term "subject" and "patient" can be used interchangeably.

In any of the embodiments of the present technology described herein, the pharmaceutical composition may be packaged in unit dosage form. The unit dosage form is effective in treating pain, schizophrenia, schizoaffective disorder, migraine, depression, pain, drug addiction, drug use, and/or drug seeking behavior. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1 \times 10^{-5}$ g/kg to 1 g/kg, preferably, $1 \times 10^{-3}$ g/kg to 1.0 g/kg. Dosage of a compound of the present technology may also vary from 0.01 mg/kg to 100 mg/kg or, preferably, from 0.1 mg/kg to 60 mg/kg. Thus, the dosage of any embodiment of a compound of the present technology may be about 0.01 mg/kg, about 0.1 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or any range including and/or in between any two of these values. Suitable unit dosage forms, include, but are not limited to powders, tablets, pills, capsules, lozenges, suppositories, patches, nasal sprays, injectibles, implantable sustained-release formulations, rnucoadherent films, topical varnishes, lipid complexes, etc.

The pharmaceutical compositions may be prepared by mixing one or more compounds of Formulas I-IV, pharmaceutically acceptable salts thereof, tautomers thereof, or solvates thereof, with pharmaceutically acceptable carriers, excipients, binders, diluents or the like to prevent and treat disorders associated with schizophrenia, schizoaffective disorder, migraine, depression, pain, drug addiction, drug use, and/or drug seeking behavior. The compounds and compositions described herein may be used to prepare formulations and medicaments that treat schizophrenia, schizoaffective disorder, migraine, depression, pain, drug addiction, drug use, and/or drug seeking behavior. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, and/or emulsifying agents may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms often include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also include, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The examples herein are provided to illustrate advantages of the present technology and to further assist a person of ordinary skill in the art with preparing or using the compounds of the present technology or salts, pharmaceutical compositions, prodrugs, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

The kappa opioid receptor (KOR) antagonist [D-Trp]CJ-15,208 (cyclo[Phe'-D-Pro-Phe$^3$-D-Trp$^4$], JVA-2802; residues are arbitrarily numbered as indicated) are modified to incorporate certain other amino acids in place of the phenylalanine and D-tryptophan residues. A variety of aromatic amino acids (D-Phe, D-Tyr, D-His, D-homophenylalalanine (D-hPhe), D-biphenylalanine (D-Bip) and regiosiomers of D-pyridylalanine (D-Pal)) have been incorporated in place of D-Trp, and heteroatom-containing amino acids (His, Pal) have been incorporated in place of Phe$^1$ or Phe$^3$ (Table 1).

TABLE 1

Analogs prepared of [D-Trp]CJ-15,208

| Substitution of D-Trp | | Substitution of Phe$^1$ | | Substitution of Phe$^3$ | |
|---|---|---|---|---|---|
| JVA # | Substitution | JVA # | Substitution | JVA # | Substitution |
| 3620 | D-Phe | 3622 | His | 3623 | His |
| 3667 | D-Bip$^a$ | 3627-3629 | Pal isomers | 3624-3626 | Pal isomers |
| 3668 | D-hPhe$^a$ | | | | |
| 3669 | D-Tyr | | | | |
| 3670 | D-His | | | | |
| 3671-3673 | D-Pal isomers | | | | |

$^a$D-Bip = D-biphenylalanine, D-hPhe = homophenylalanine

These macrocyclic peptides of the present technology were synthesized by a combination of solid phase synthesis of the linear peptide precursors, followed by cleavage of the peptides from the resin and cyclization in solution. The peptides were purified by normal phase flash column chromatography and analyzed by analytical HPLC and mass spectrometry.

The analogs were evaluated in vivo in an analgesic assay (mouse 55° C. warm-water tail withdrawal assay) for opioid agonist and antagonist activity. Representative analogs were evaluated in a conditioned place preference (CPP) assay for their ability to prevent stress-induced relapse to cocaine-seeking behavior. Further, representative analogs were evaluated for opioid receptor affinity in radioligand binding assays (Table 2). As illustrated further herein, macrocyclic peptides of the present technology exhibit good pharmacological activity in vivo.

TABLE 2

Opioid receptor affinities of representative macrocyclic tetrapeptides

| JVA # | Substitution from JVA-2802 | KOR $K_i$ (nM ± SEM) | MOR $K_i$ (nM ± SEM) | Selectivity (KOR/MOR) |
|---|---|---|---|---|
| 2802 $^a$ | — | 21.8 ± 4.8 (8) | 259 ± 29 | 1/12 |
| | D-Trp$^4$ substitution: | | | |
| 3620 $^a$ | D-Phe | 28.9 ± 4.9 | 1100 ± 80 | 1/38 |
| | Phe$^1$ substitution: | | | |
| 3622 $^a$ | His | 667 ± 470 | 2500 ± 510 | 1/3.7 |
| 3627 $^a$ | 2'-Pal | 58.4 ± 9.3 | 2530 ± 460 | 1/43 |
| 3628 $^a$ | 3'-Pal | 41.8 ± 16.3 | 988 ± 146 | 1/24 |
| 3629 $^a$ | 4'-Pal | 32.0 ± 4.1 | 2740 ± 310 | 1/86 |

TABLE 2-continued

Opioid receptor affinities of representative macrocyclic tetrapeptides

| JVA # | Substitution from JVA-2802 | KOR $K_i$ (nM ± SEM) | MOR $K_i$ (nM ± SEM) | Selectivity (KOR/MOR) |
|---|---|---|---|---|
| | Phe$^3$ substitution: | | | |
| 3623 [a] | His | 67.7 ± 9.2 | 366 ± 98 | 1/5.4 |
| 3624 [a] | 3'-Pal | 8.34 ± 1.48 | 191 ± 39 | 1/23 |
| 3625 [a] | 4'-Pal | 30.7 ± 6.8 | 371 ± 81 | 1/12 |
| 3626 [a] | 2'-Pal | 82.3 ± 13.8 | 1610 ± 590 | 1/20 |

[a] The analogs exhibit minimal binding ($K_i$ > 10 μM) at DOR.

Figure 1B:
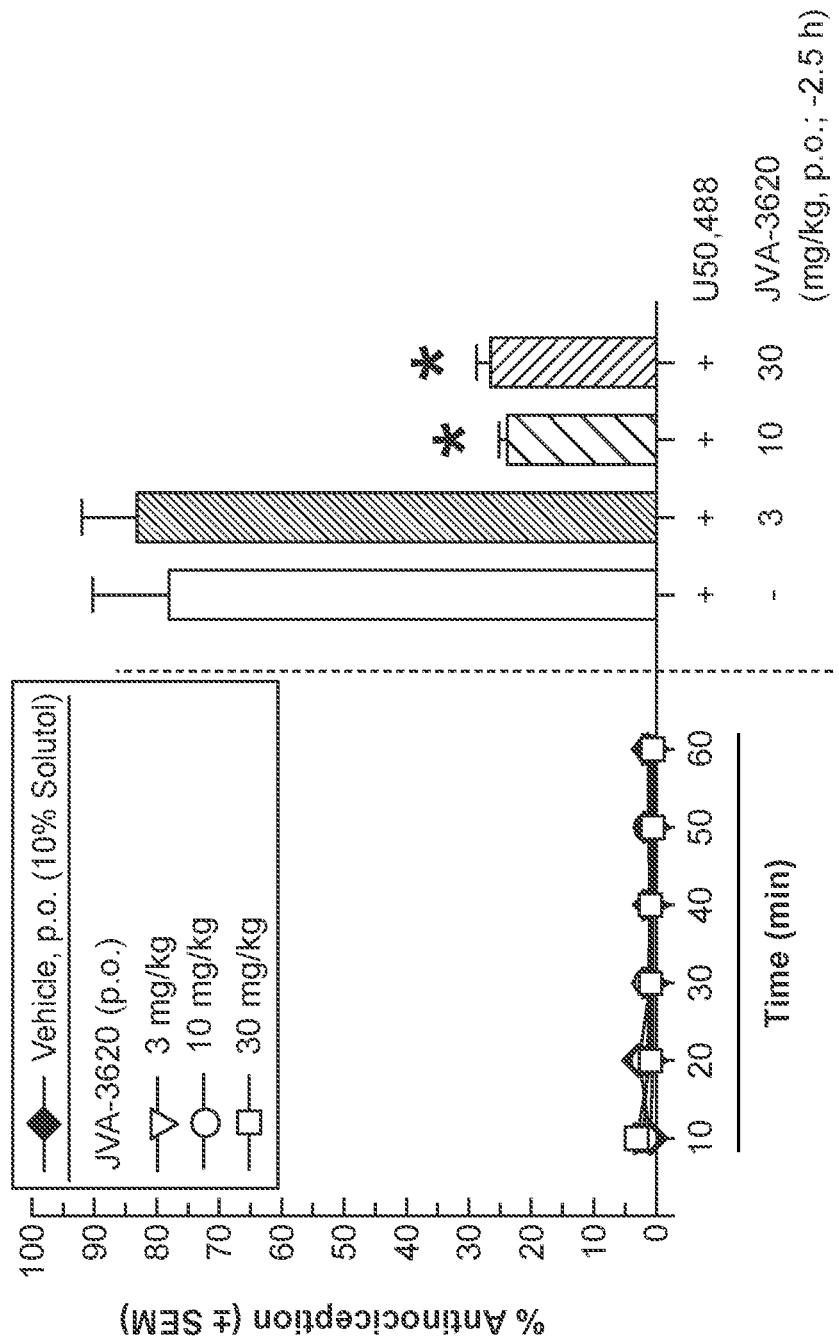
Figure 1C:
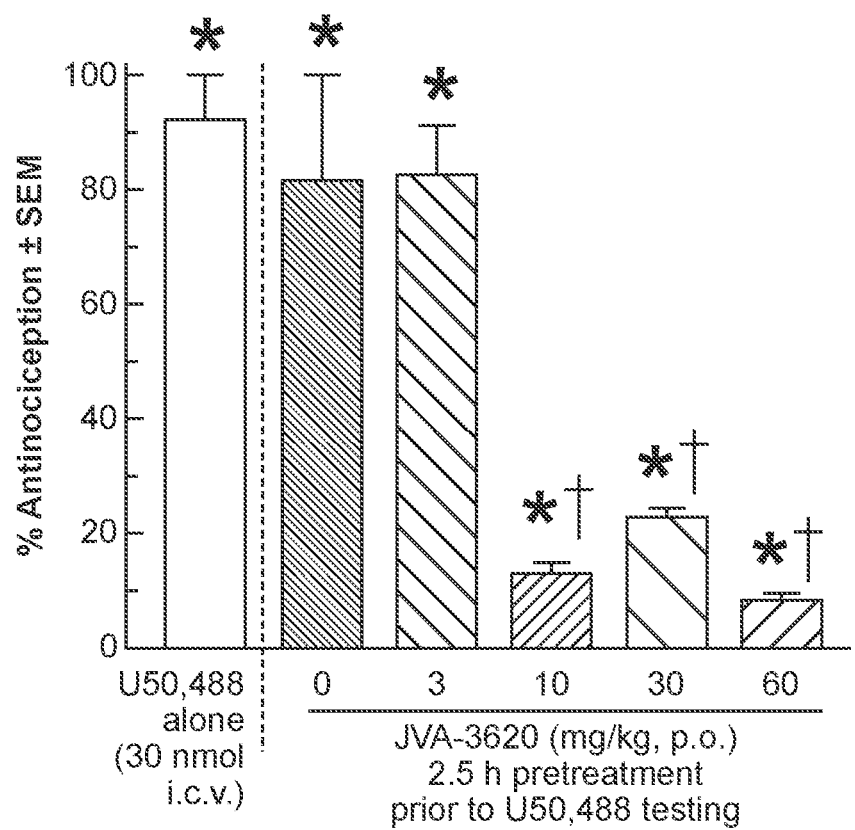
Figure 1D:
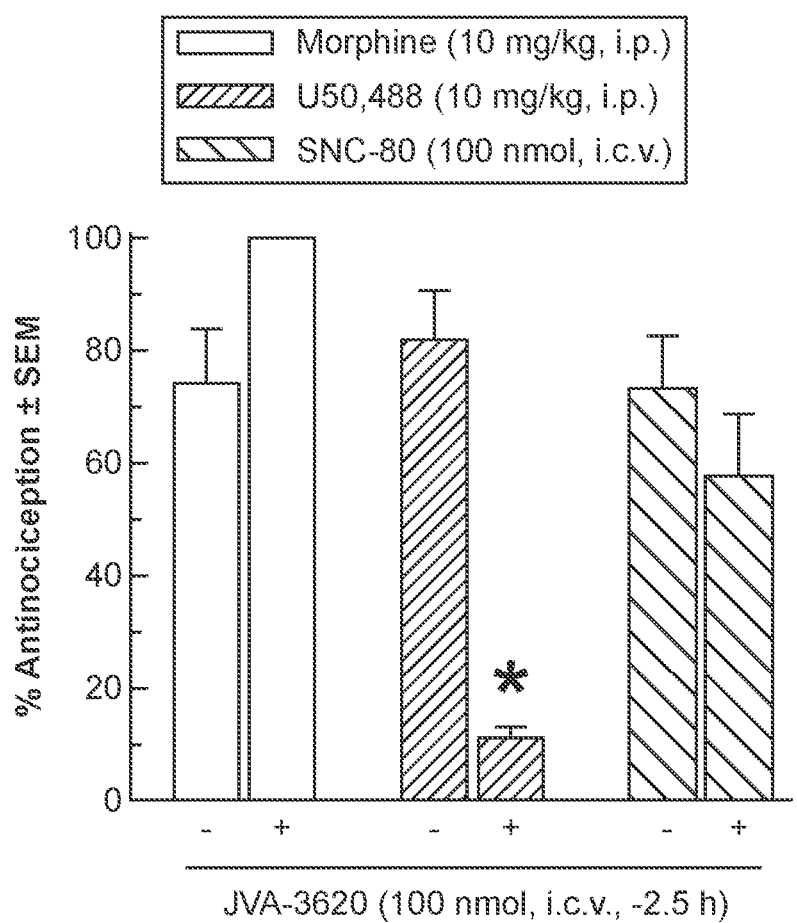
Figure 1E:
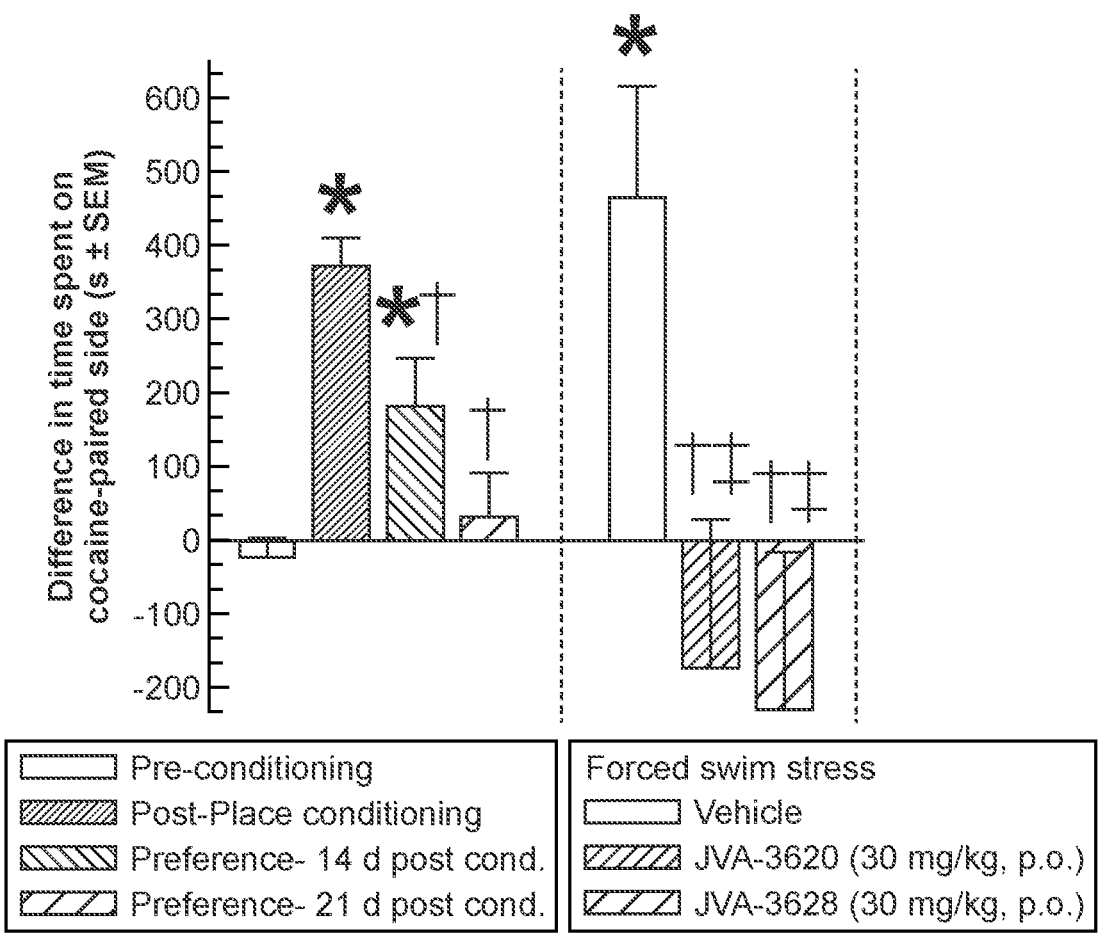
Figure 4:
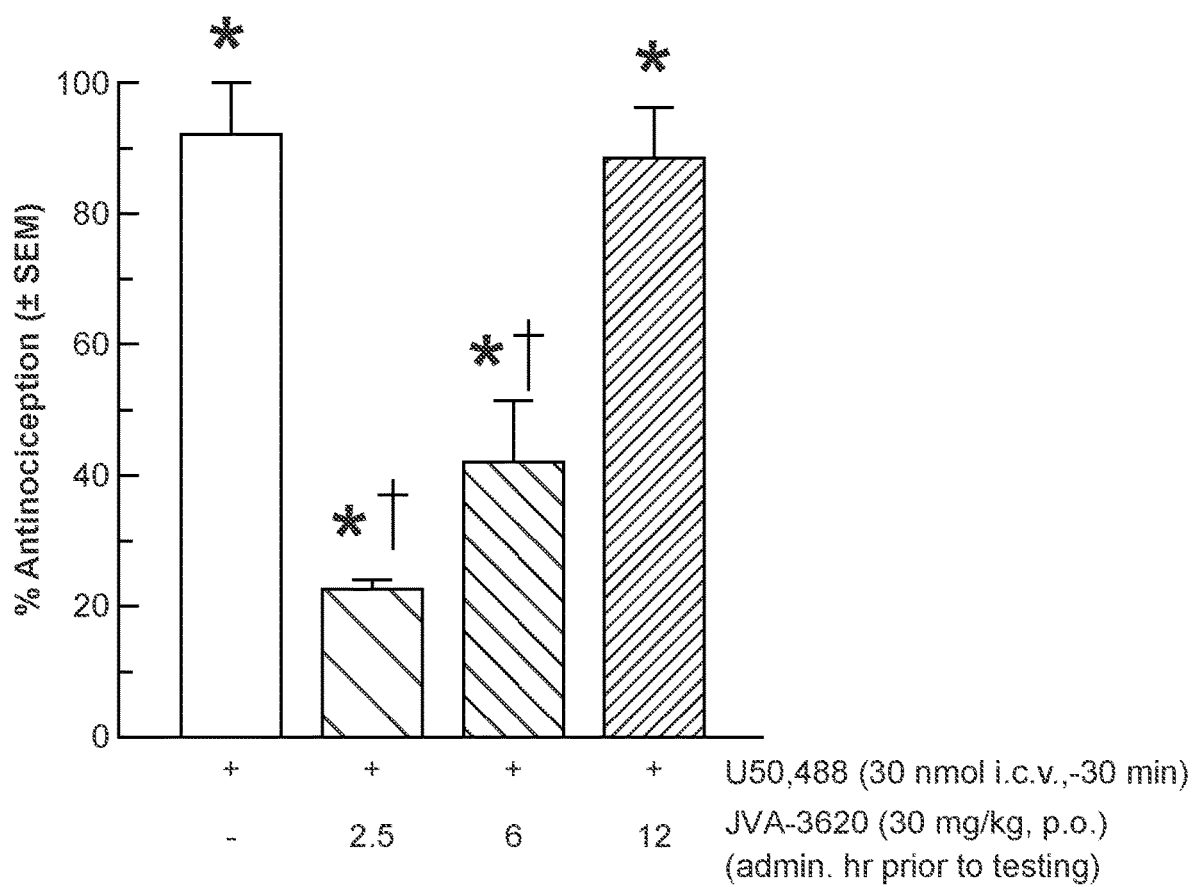
FIG. 4 provides the results of studies with JVA-3620 showing that, following oral administration (30 mg/kg p.o.), JVA-3620 exhibits kappa opioid receptor (KOR) antagonism of centrally administered KOR agonist activity (produced by U50,488 administered intracerebroventricularly (i.c.v.)) lasting 6-12 hours.
Figure 6A:
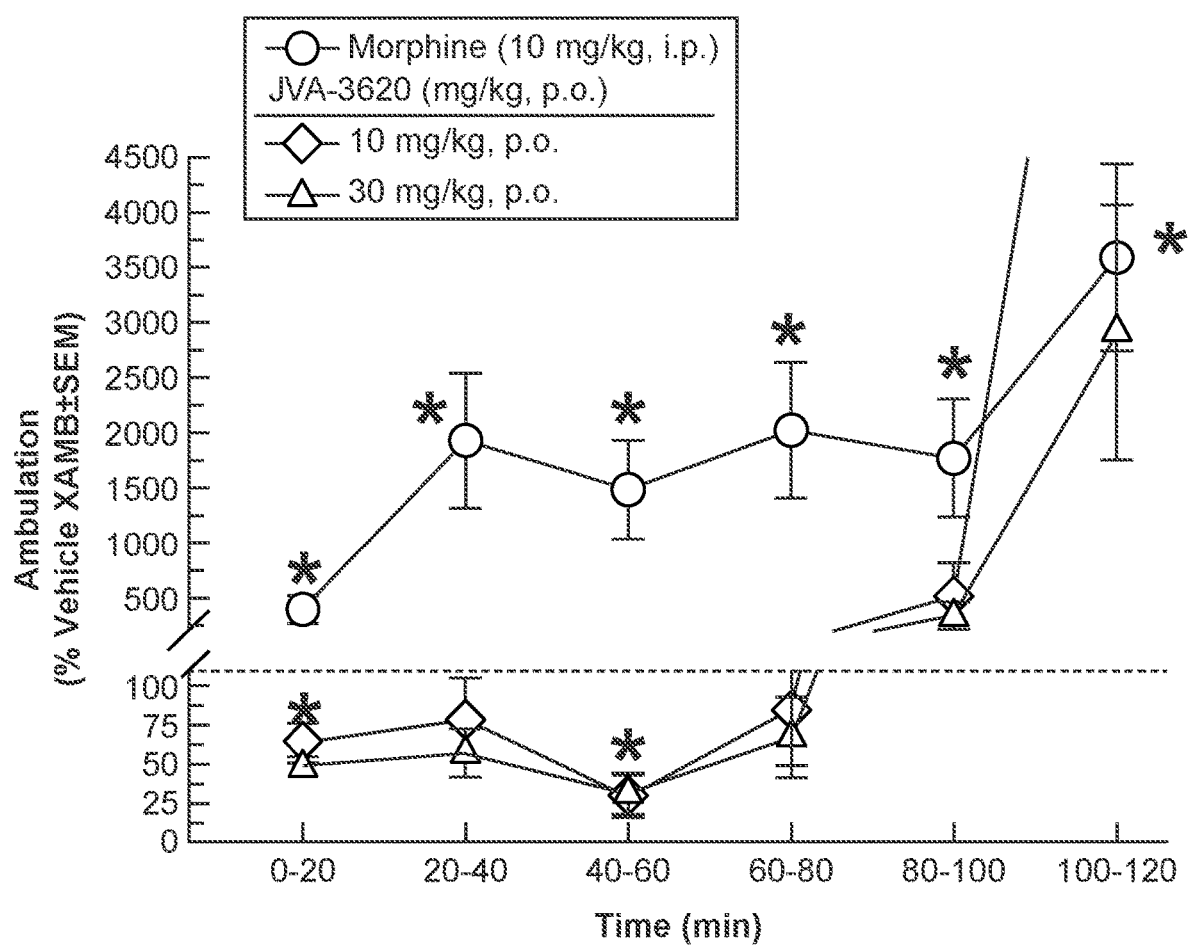
FIGS. 6A-B provides the results of studies on locomotion and respiration following oral administration of JVA-3620.
Figure 6B:
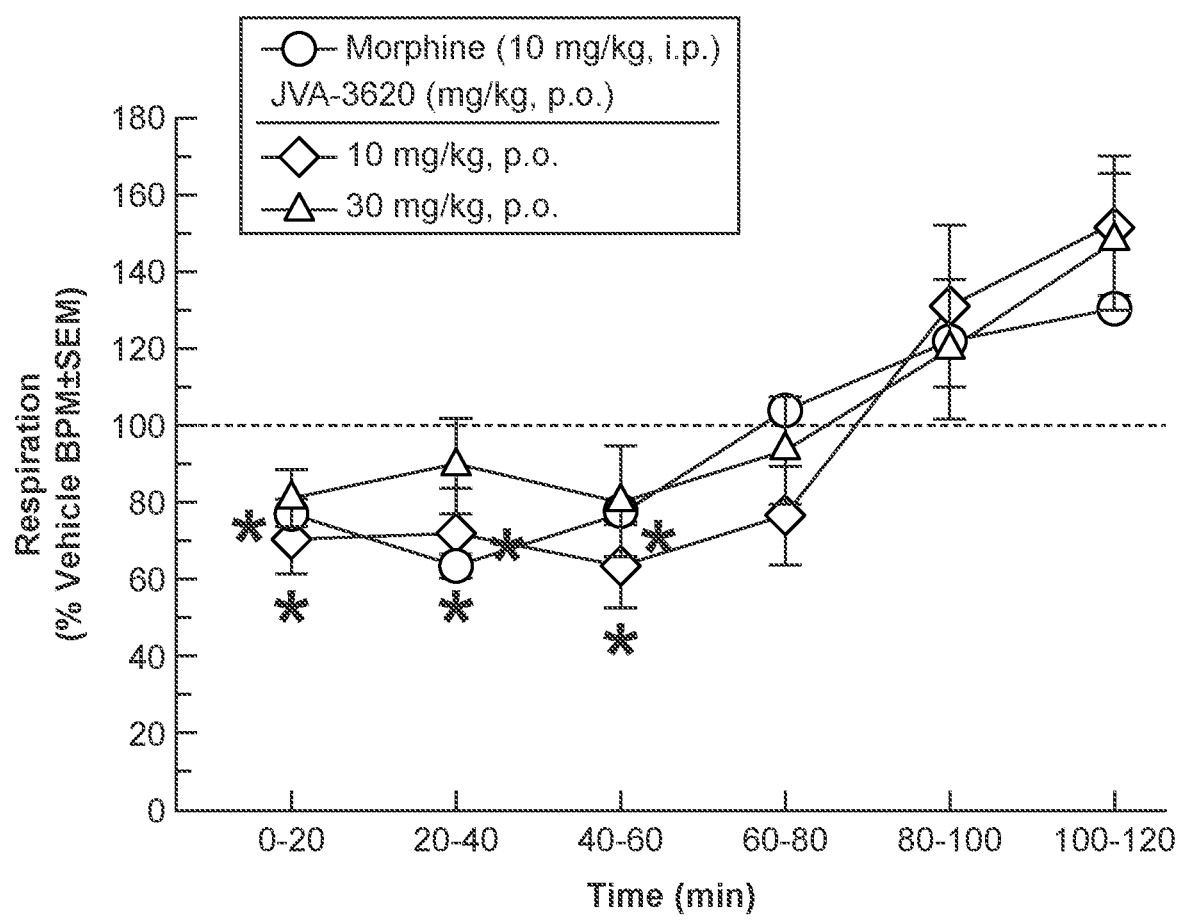

Substitutions for D-Trp$^4$: The D-Phe$^4$ analog (JVA-3620) surprisingly exhibited KOR antagonism after both direct (intracerebroventricular, i.c.v.) injection into the brain (FIG. 1A) and oral administration (FIG. 1B). Orally administered JVA-3620 antagonized centrally (i.c.v.) administered KOR agonist (FIG. 1C), indicating that the D-Phe$^4$ analog penetrates the blood-brain-barrier to reach KOR in the brain; the oral dose of this peptide required to significantly antagonize centrally administered U50,488 (10 mg/kg) was less than that of [D-Trp]CJ-15,208 (30 mg/kg, Eans et al., 2013). JVA-3620 selectively antagonized the KOR agonist U50, 488, but not the mu opioid receptor agonist morphine or the delta opioid receptor antagonist SNC-80 (FIG. 1D). Orally administered JVA-3620 prevented stress-induced relapse of cocaine-seeking behavior in the CPP assay at a lower dose (30 mg/kg, FIG. 1E) than [D-Trp]CJ-15,208 (60 mg/kg, Eans et al., 2013). Following oral administration (30 mg/kg p.o.), JVA-3620 exhibits kappa opioid receptor (KOR) antagonism of centrally administered KOR agonist activity (produced by U50,488 administered intracerebroventricularly (i.c.v.)) lasting 6-12 hours (FIG. 4). Other analogs with substitution at this position (e.g., the D-Pal$^4$ compounds) exhibited antinociception (agonist activity) with variable KOR antagonism. Further, FIG. 6A illustrates that orally administered (10 or 30 mg/kg p.o.) JVA-3620 does not produce hyperlocomotion like morphine, but instead can significantly decrease locomotion during the first hour. FIG. 6B illustrates that JVA-3620 decreases respiration during the first hour, but whether or not such decreased respiration is related to the decreased locomotion is unknown from this data.

Figure 2A:
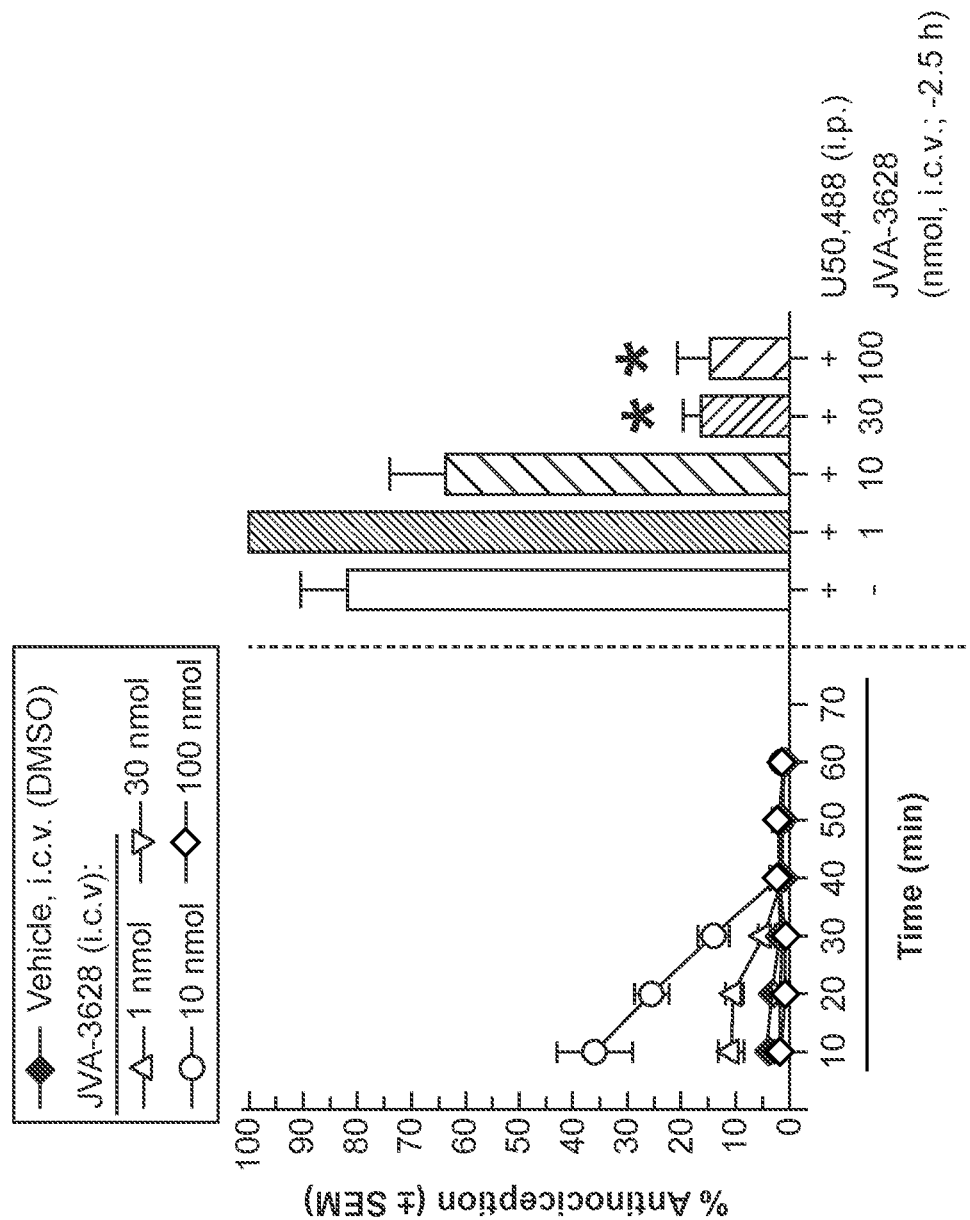
FIGS. 2A-E provides in vivo data for JVA-3628 (a compound of the present technology) in mice.
Figure 2B:
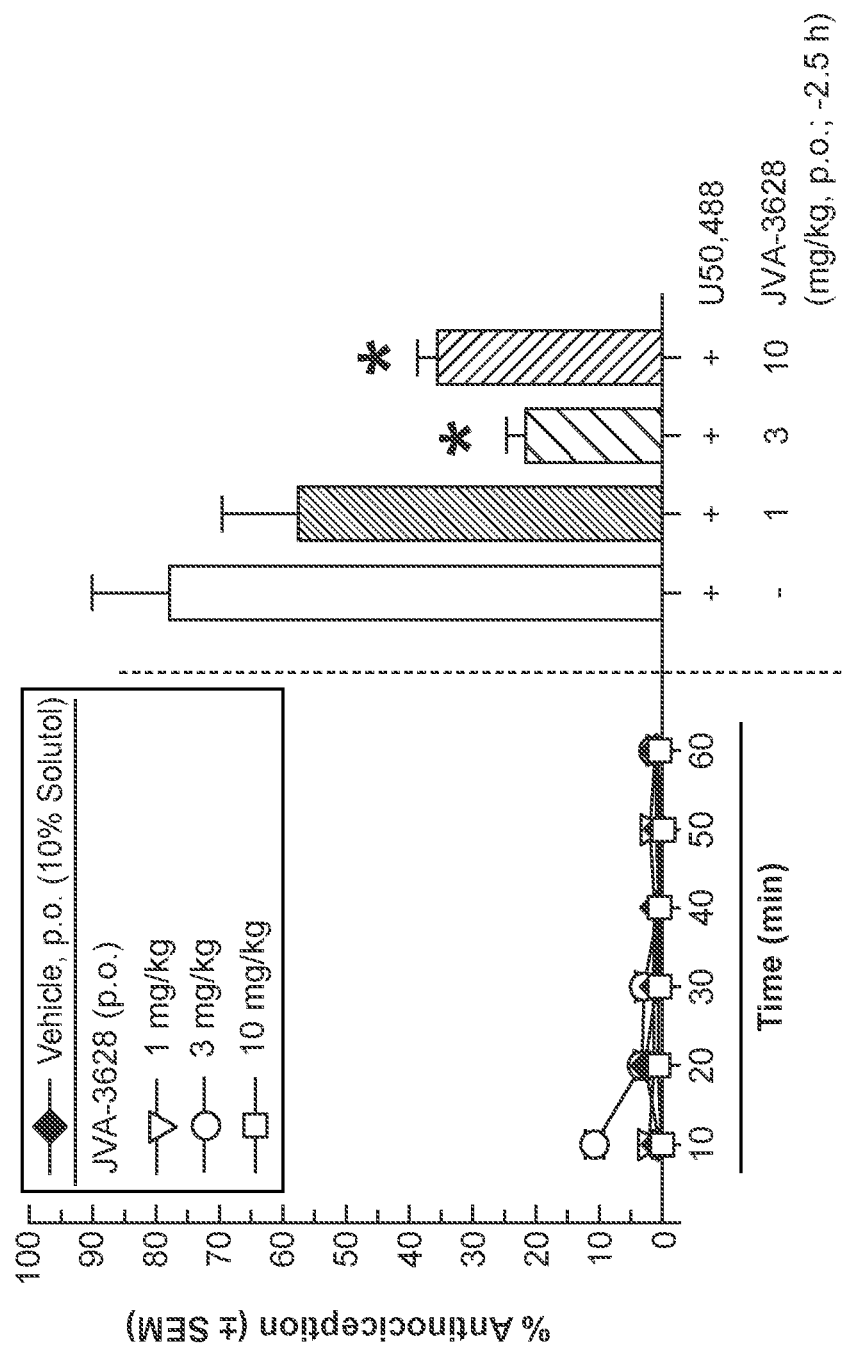
Figure 2C:
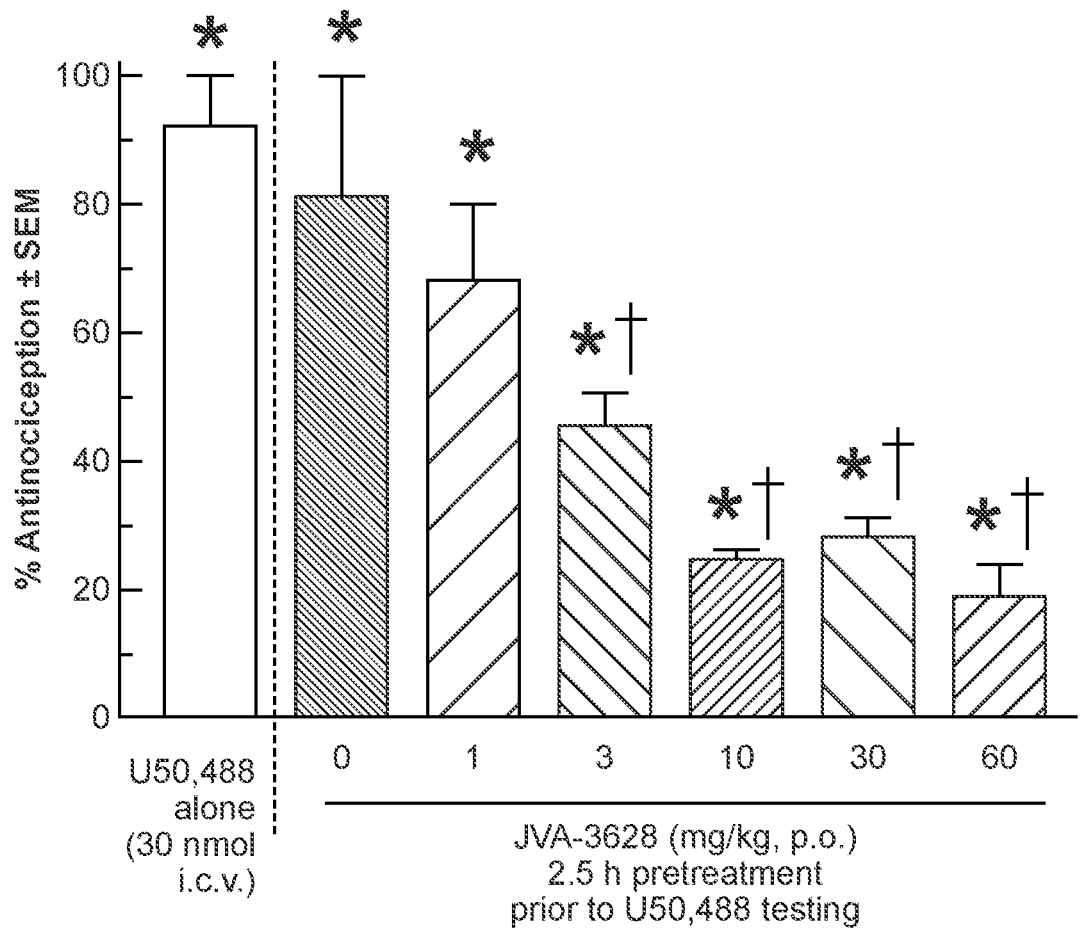
Figure 2D:
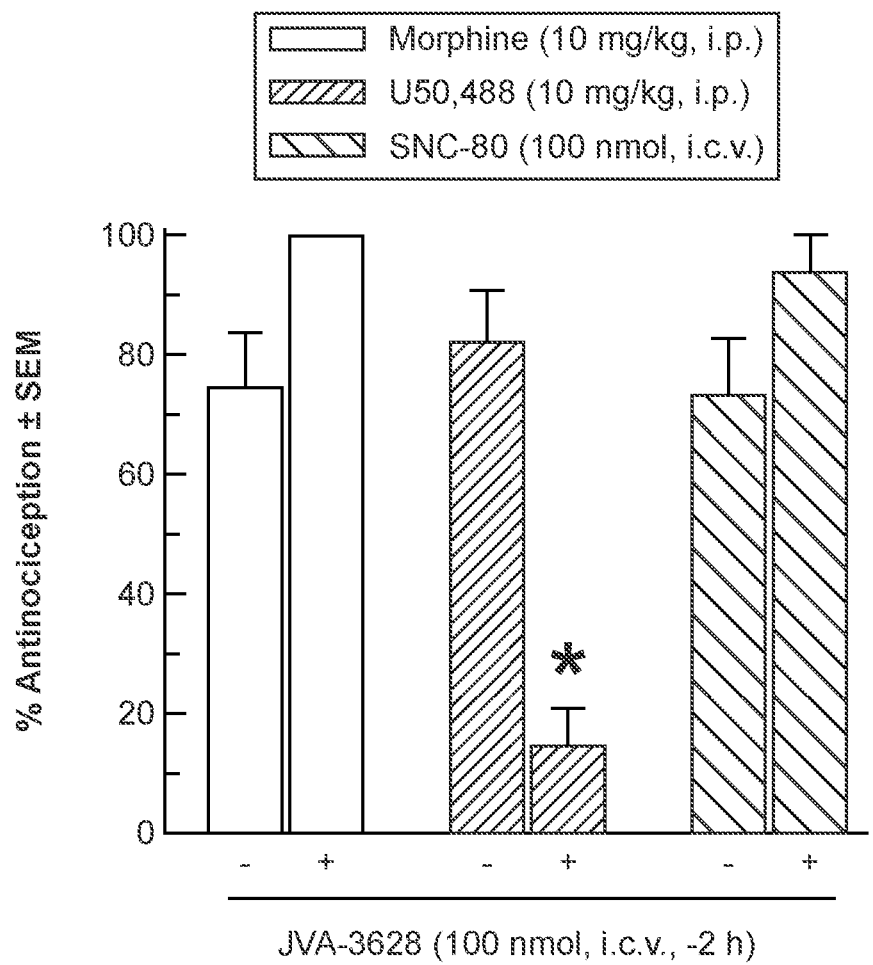
Figure 2E:
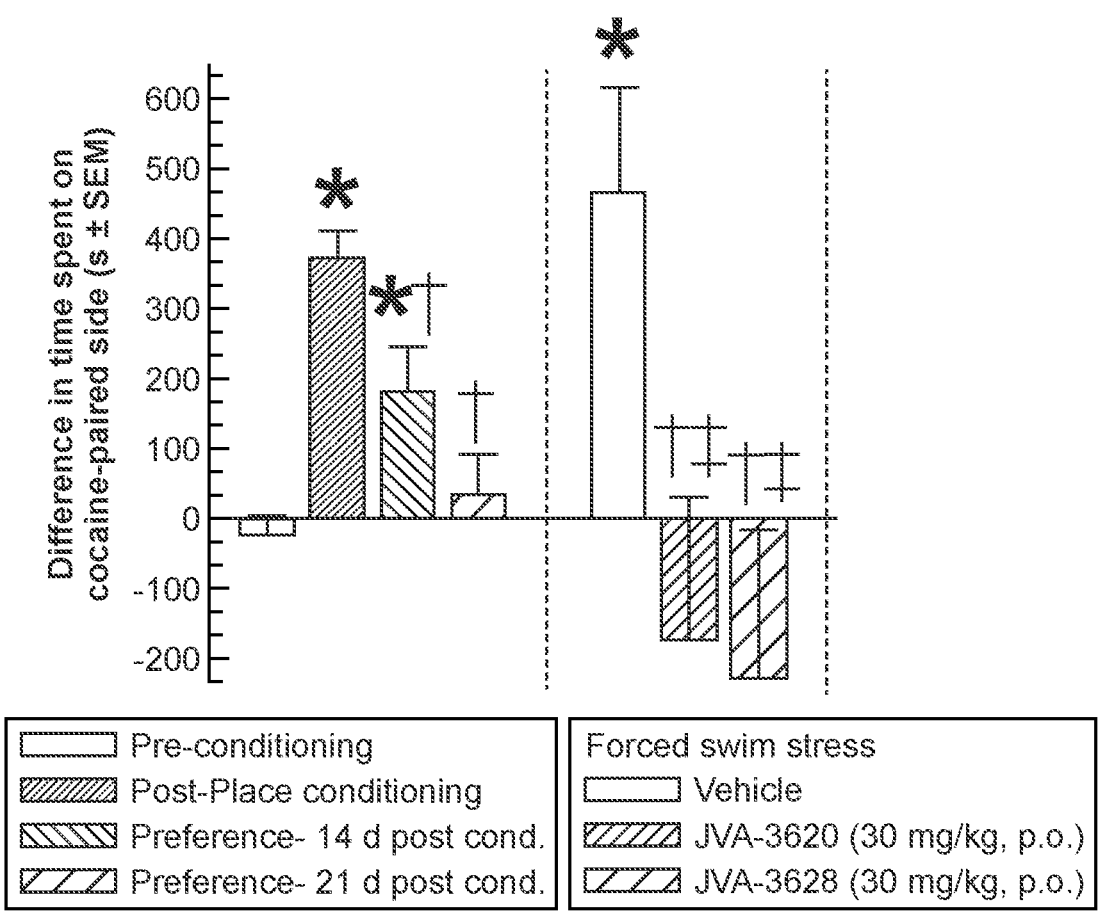
Figure 3:
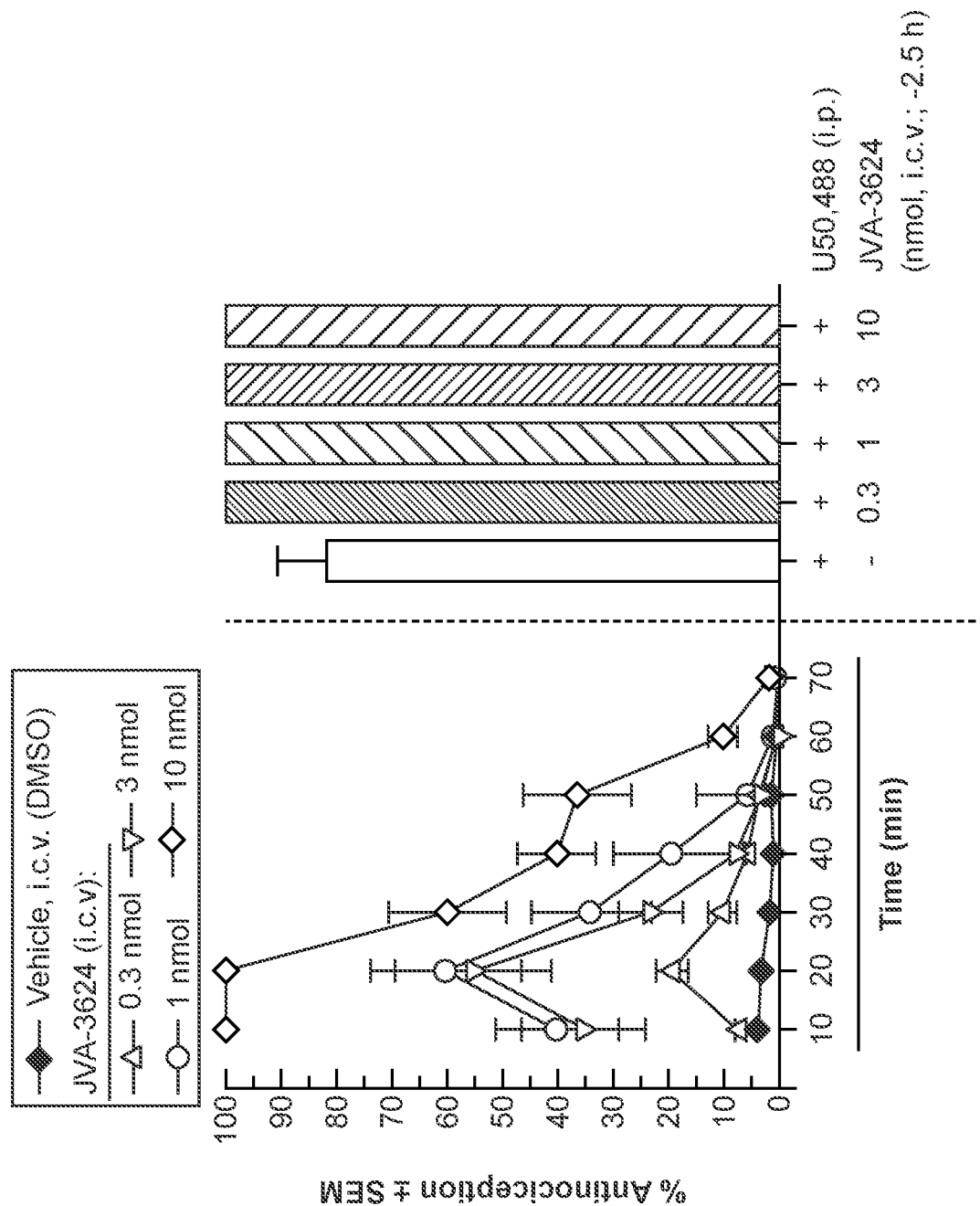
FIG. 3 provides the results of studies showing JVA-3624 (a compound of the present technology) exhibits antinociception (agonist activity, $ED_{50}$=1.13 nmol i.c.v.; left side), but not KOR antagonism (right side).
Figure 5:
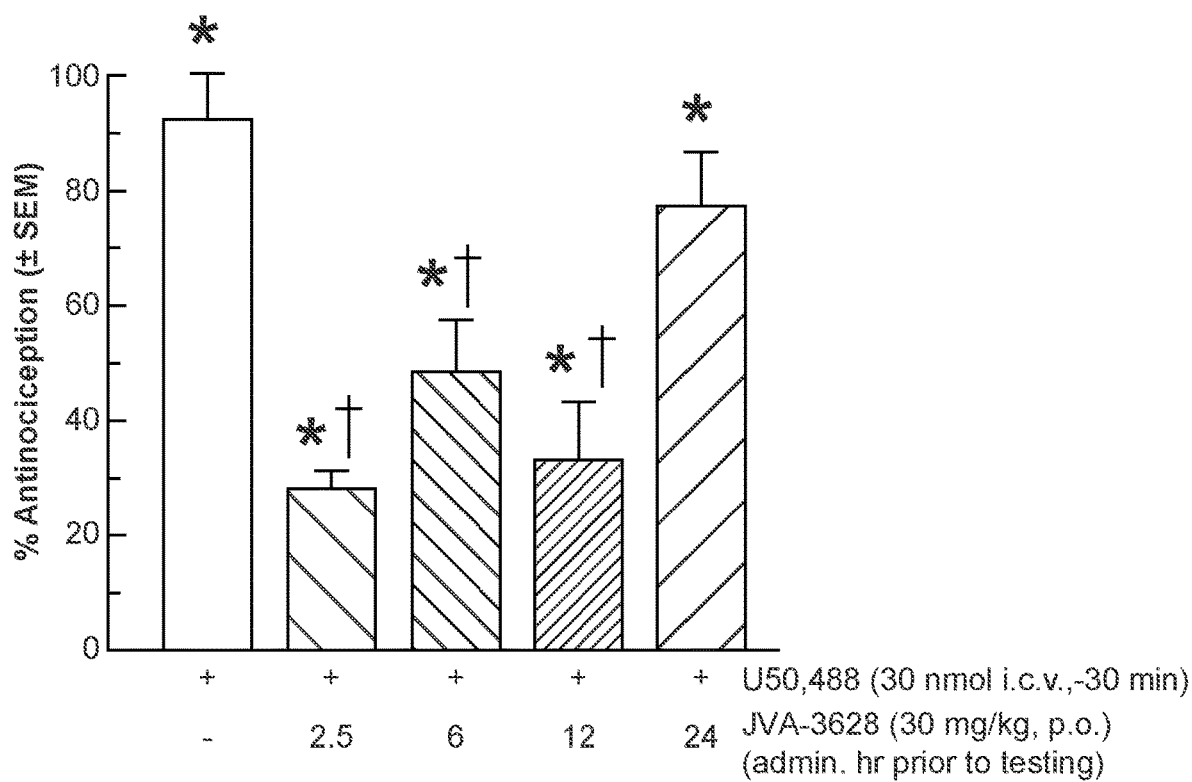
FIG. 5 provides the results of studies with JVA-3628 (a compound of the present technology) showing that, following oral administration (30 mg/kg p.o.), JVA-3628 exhibits kappa opioid receptor (KOR) antagonism of centrally administered KOR agonist activity (produced by U50,488 administered intracerebroventricularly (i.c.v.)) lasting 12-24 hours.
Figure 7A:
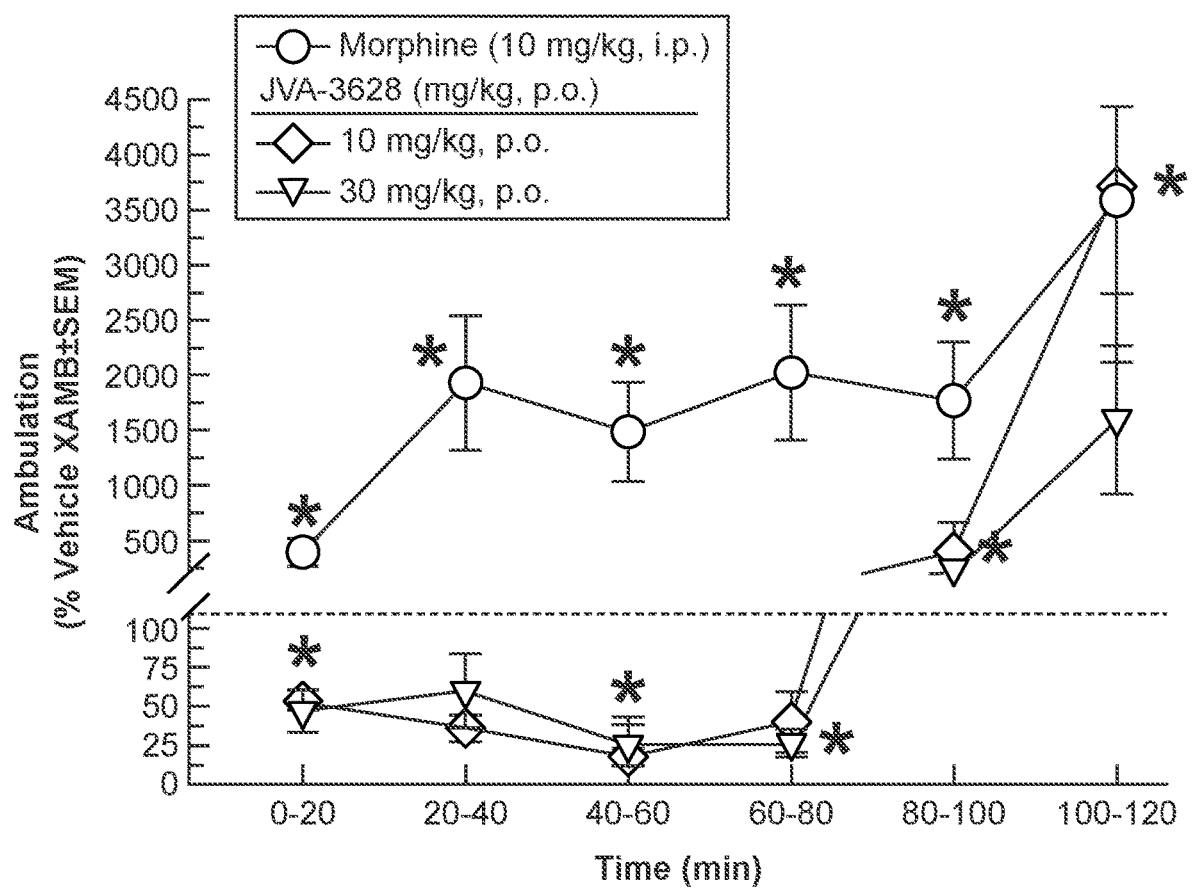
FIG. 7A-B provides the results of studies on locomotion and respiration following oral administration of JVA-3628.
Figure 7B:
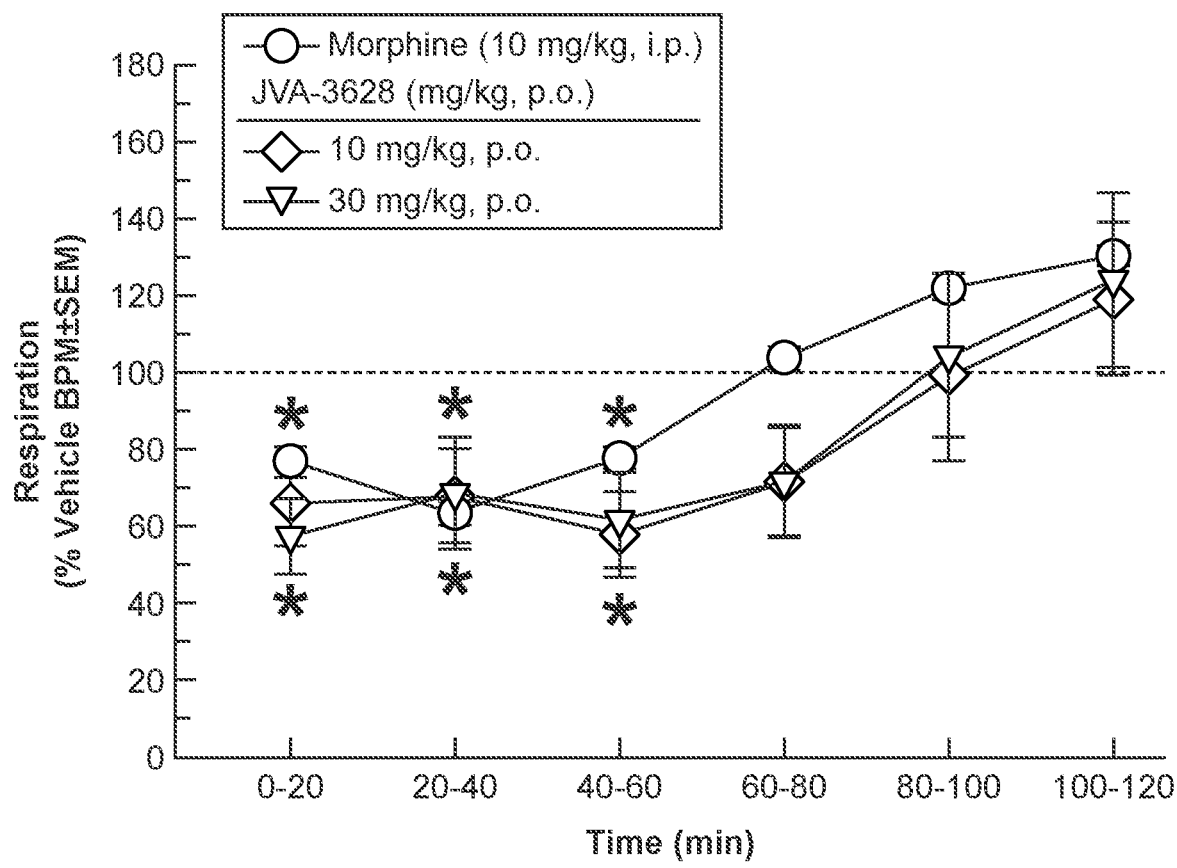

Substitutions for the Phe$^1$ and Phe$^4$ residues: The 3'-Pal$^1$ analog (JVA-3628) surprisingly exhibited an activity profile similar to that of the D-Phe$^4$ analog, exhibiting selective KOR antagonism after i.c.v. administration (FIGS. 2A and 2D), antagonizing both peripherally and administered KOR agonist after oral administration (FIGS. 2B and 2C), and preventing stress-induced relapse of cocaine-seeking behavior after oral administration at 30 mg/kg (FIG. 2E). Following oral administration (30 mg/kg p.o.), JVA-3628 exhibits kappa opioid receptor (KOR) antagonism of centrally administered KOR agonist activity (produced by U50,488 administered intracerebroventricularly (i.c.v.)) lasting 12-24 hours (FIG. 5). In addition, orally administered (10 or 30 mg/kg p.o.) JVA-3628 does not produce hyperlocomotion like morphine, but instead can significantly decrease locomotion during the first hour (FIG. 7A); FIG. 7B illustrates that JVA-3628 decreases respiration during the first hour, but whether or not such decreased respiration is related to the decreased locomotion is unknown from this data. In contrast, the Phe$^3$ substituted analogs were potent agonists, but unexpectedly did not exhibit KOR antagonism (see, e.g., FIG. 3).

Figure 8:
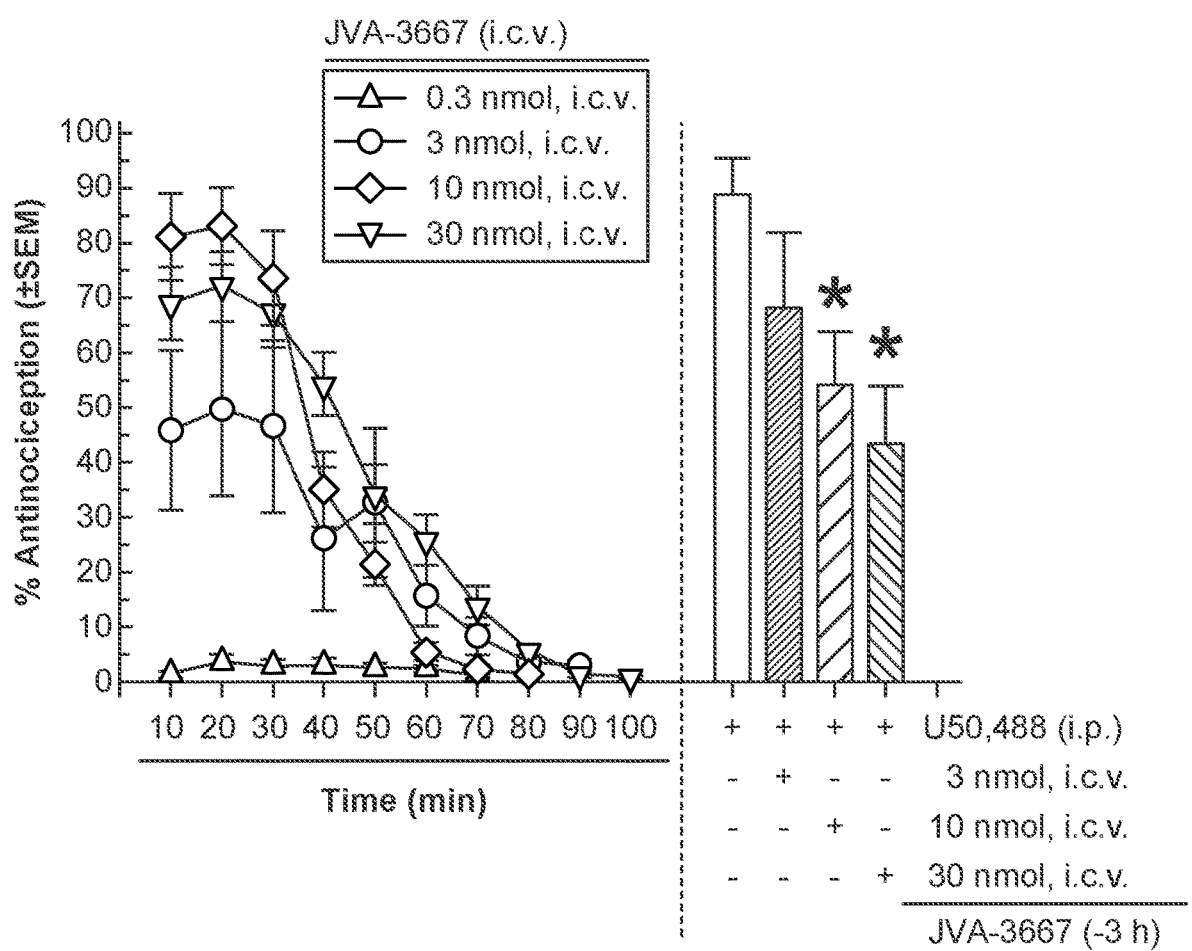
FIG. 8 provides the results of studies showing [D-Bip$^4$] CJ-15,208 (JVA-3667; a compound of the present technology) exhibits mixed agonist/weak KOR antagonist activity following i.c.v. administration.
Figure 9:
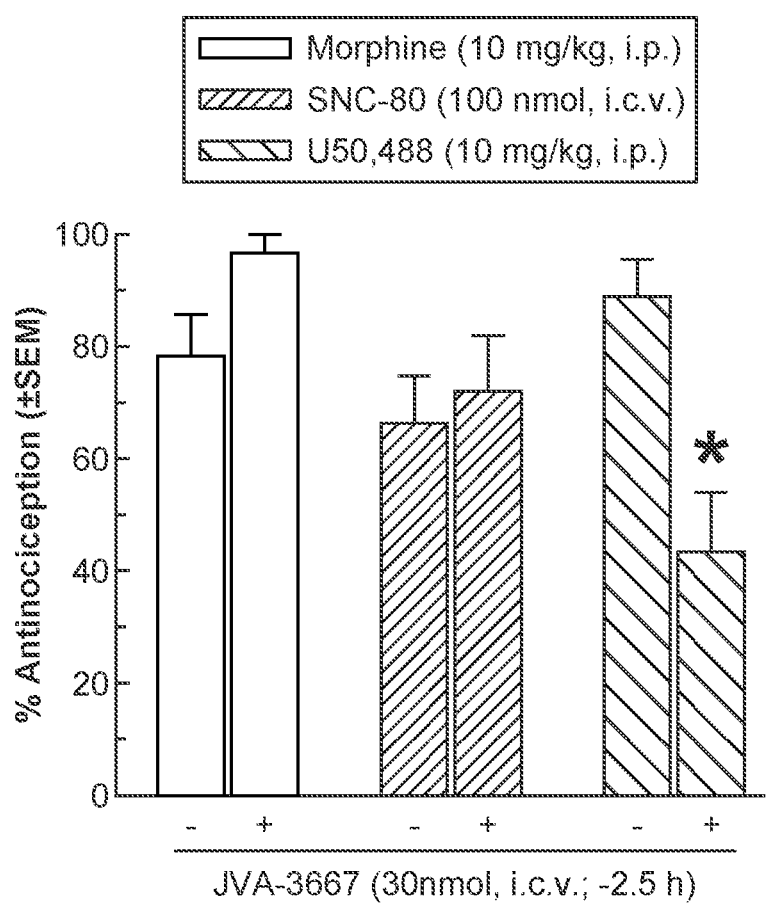
FIG. 9 provides the results of studies showing the antagonist activity of JVA-3667 is selective for KOR.
Figure 10:
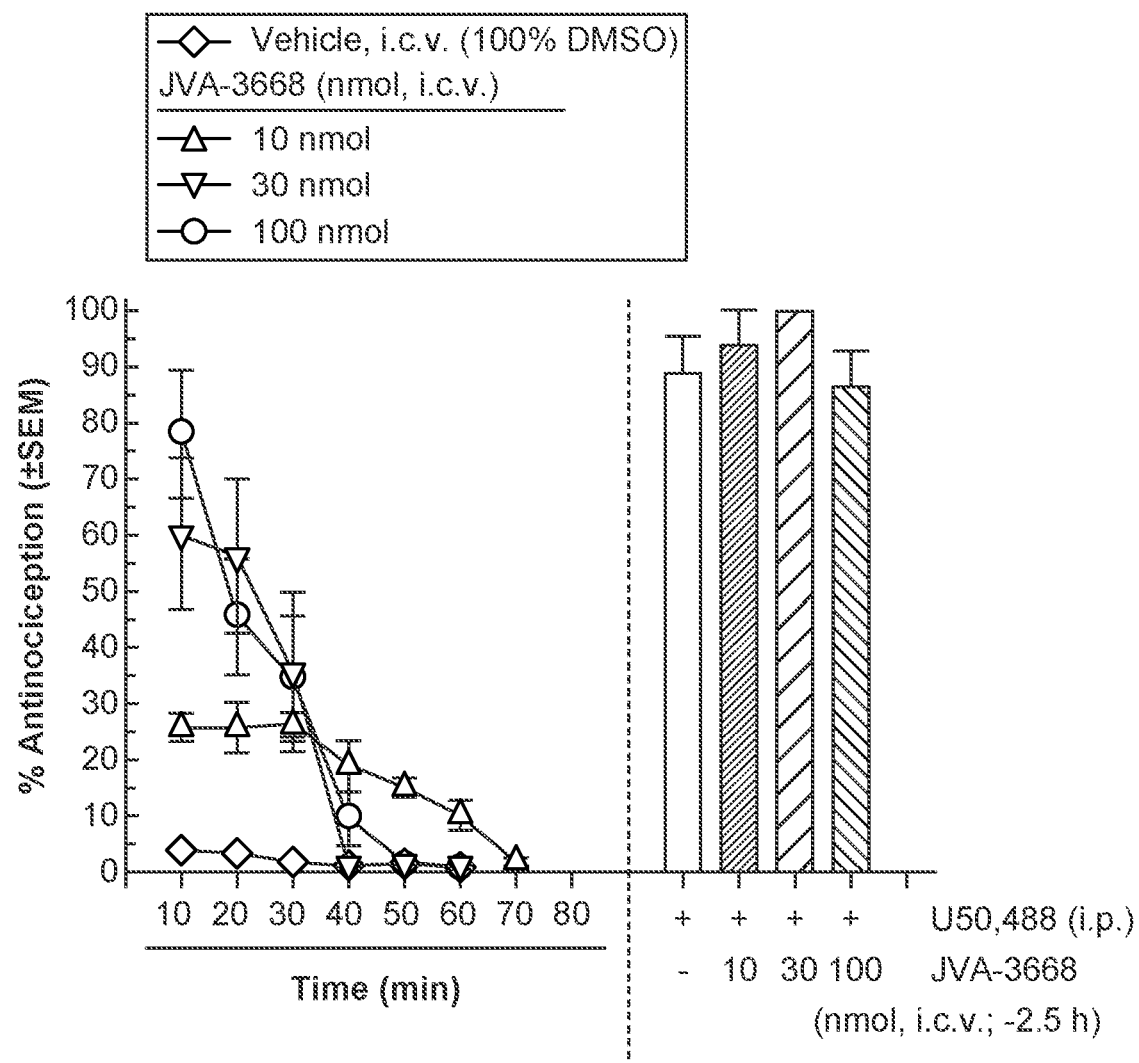
FIG. 10 provides the results of studies showing [D-hPhe$^4$] CJ-15,208 (JVA-3668; a compound of the present technology) exhibits agonist, but not KOR antagonist, activity after i.c.v. administration.
Figure 11:
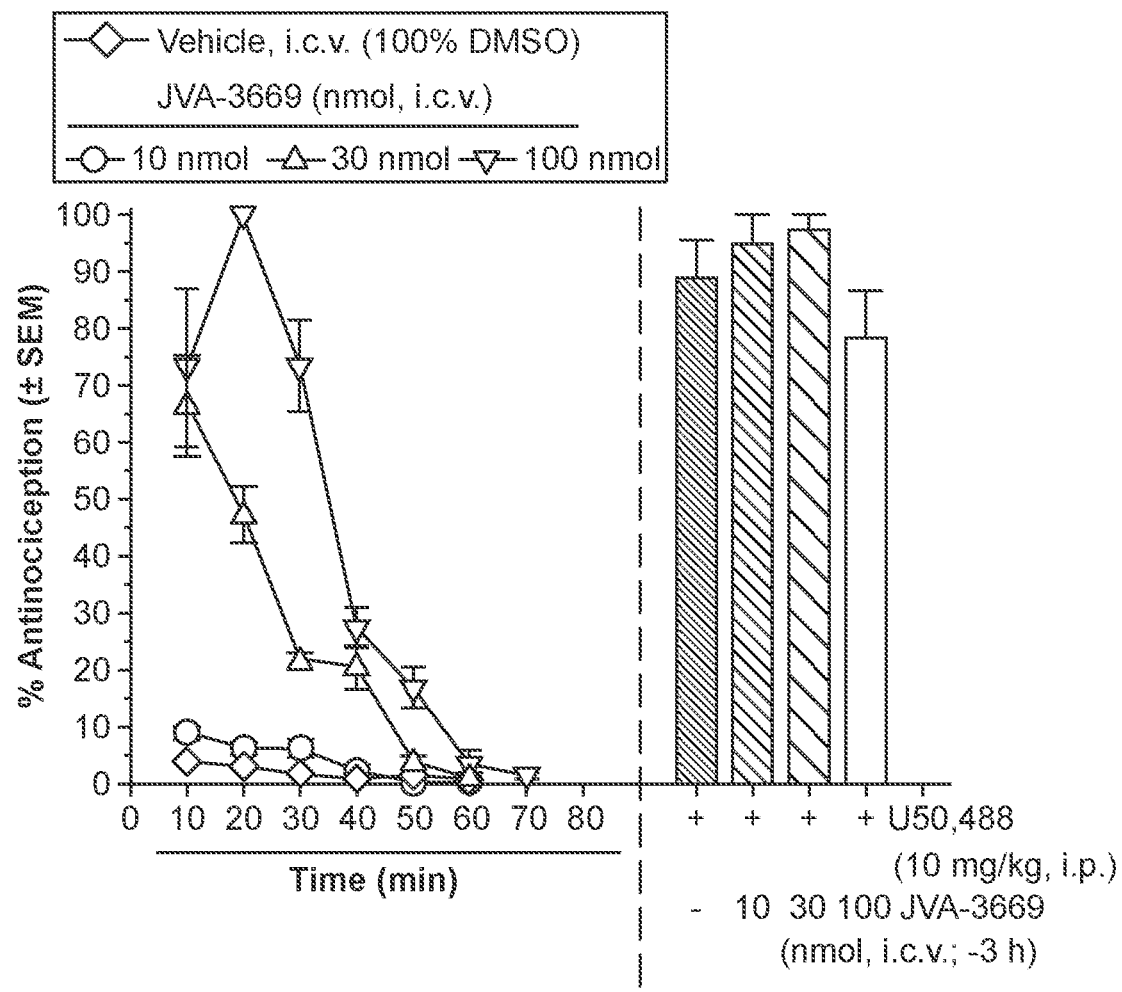
FIG. 11 provides the results of studies showing [D-Tyr$^4$] CJ-15,208 (JVA-3669; a compound of the present technology) exhibits agonist, but not KOR antagonist, activity after i.c.v. administration.
Figure 12:
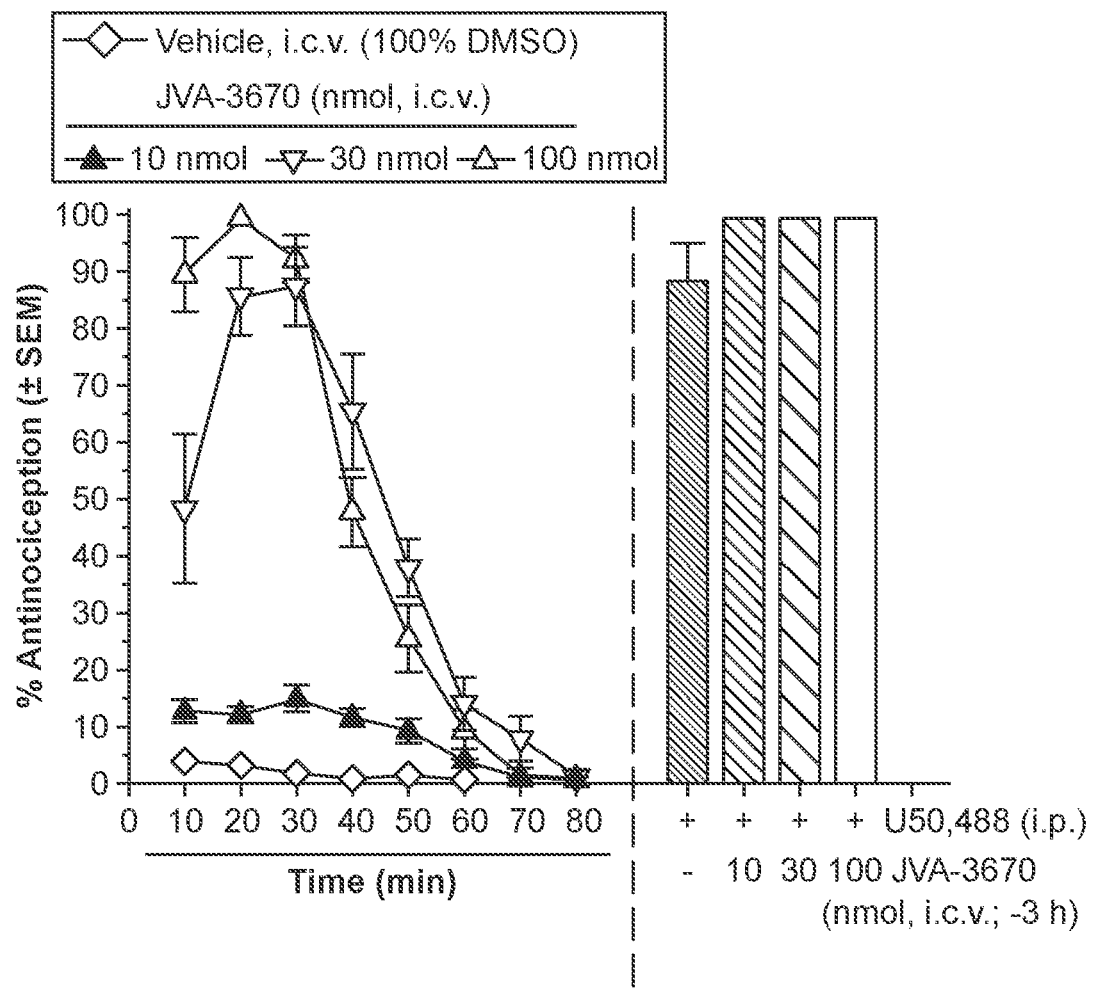
FIG. 12 provides the results of studies showing [D-His$^4$] CJ-15,208 (JVA-3670; a compound of the present technology) exhibits agonist, but not KOR antagonist, activity after i.c.v. administration.
Figure 13:
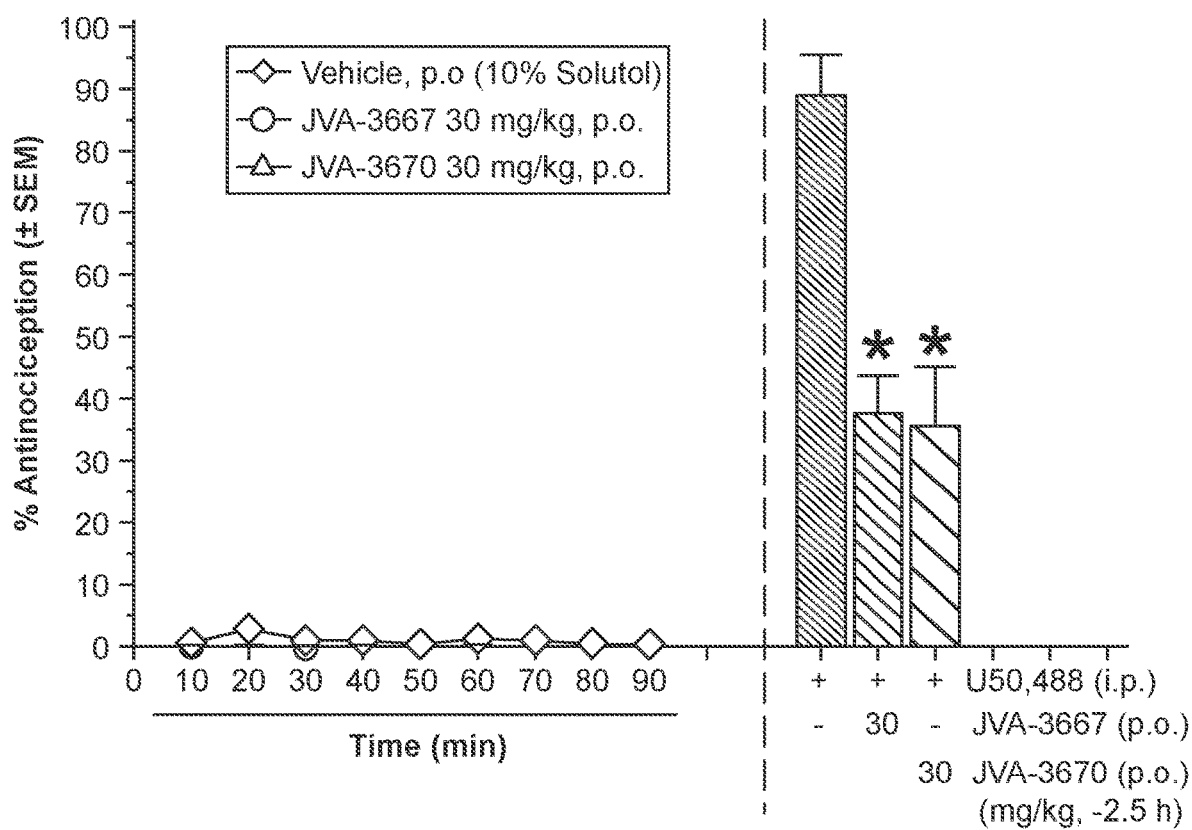
FIG. 13 provides the results of studies showing [D-Bip$^4$] CJ-15,208 (JVA-3667) and [D-His$^4$]CJ-15,208 (JVA-3670) each exhibit KOR antagonism after oral administration.

[D-Bip$^4$]CJ-15,208 (JVA-3667) exhibits mixed agonist/weak KOR antagonist activity following i.c.v. administration (FIG. 8), where the antagonist activity of JVA-3667 is selective for KOR (FIG. 9). [D-hPhe$^4$]CJ-15,208 (JVA-3668), [D-Tyr$^4$]CJ-15,208 (JVA-3669), and [D-His$^4$]CJ-15, 208 (JVA-3670) each exhibit agonist, but not KOR antagonist, activity after i.c.v. administration (respectively, FIGS. 10, 11, 12). Yet interestingly, after oral administration, each of [D-Bip$^4$]CJ-15,208 (JVA-3667) and [D-His$^4$]CJ-15,208 (JVA-3670) exhibit only KOR antagonism (FIG. 13).

Figure 14A:
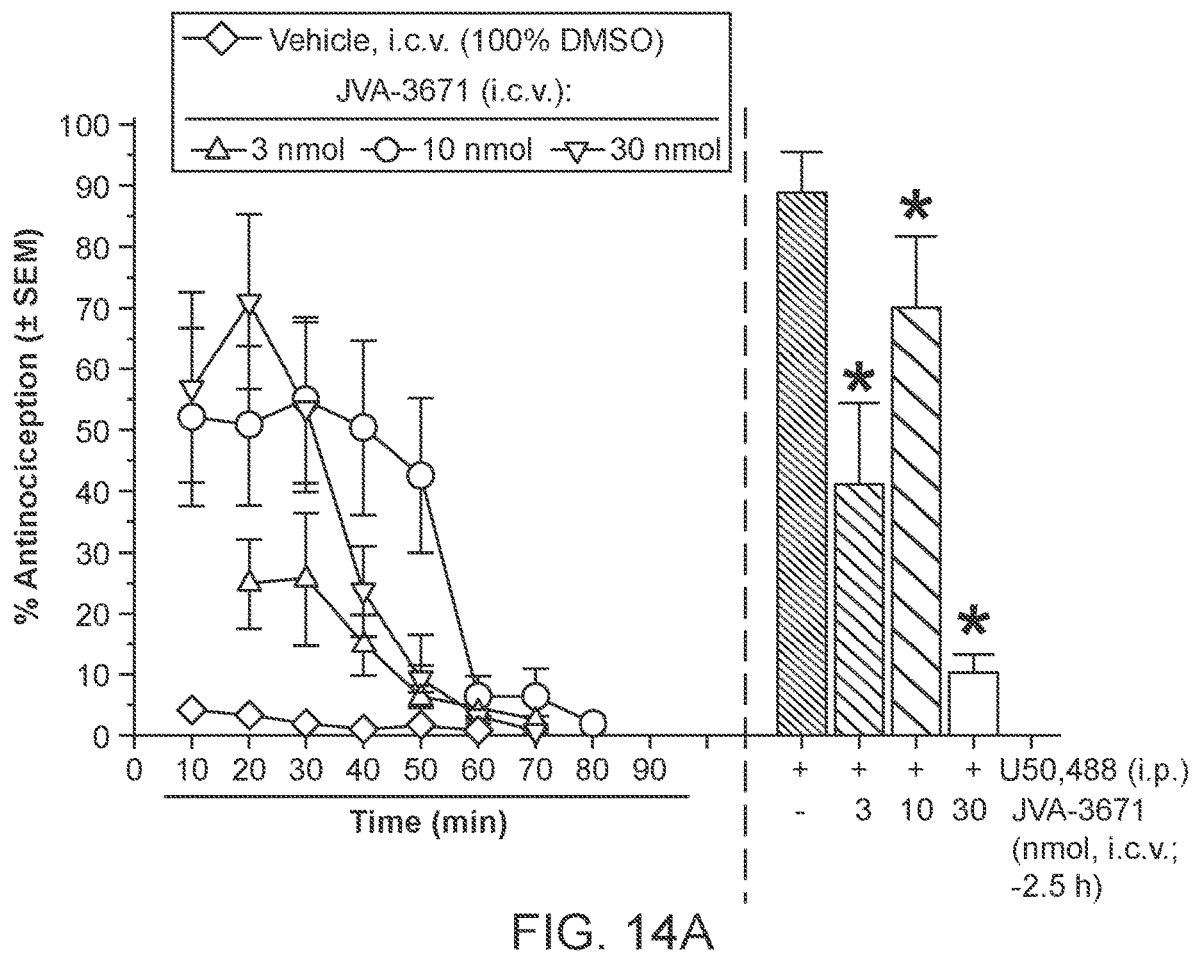
FIGS. 14A-C provide the results of studies showing that, following central (i.c.v.) administration, [D-2'-Pal$^4$]CJ-15,208 (JVA-3671; a compound of the present technology) exhibits antinociception (FIG. 14A) mediated by delta opioid receptors (DOR)(FIG. 14B) and also exhibits KOR antagonist activity (FIG. 14C).
Figure 14B:
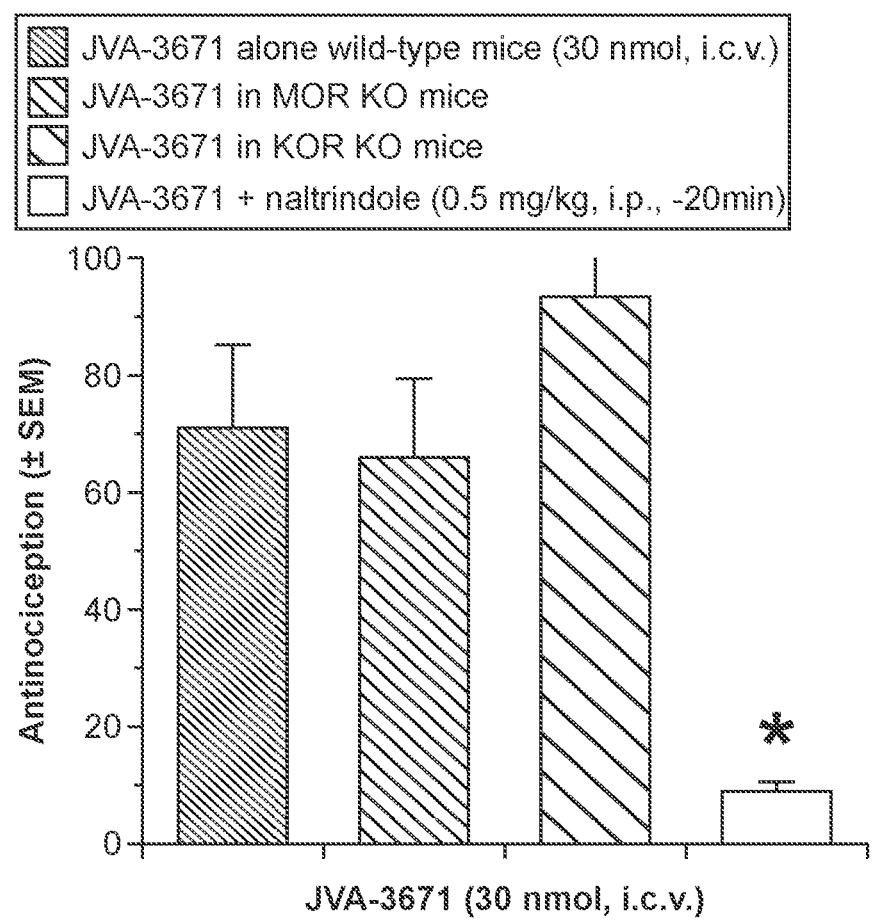
Figure 14C:
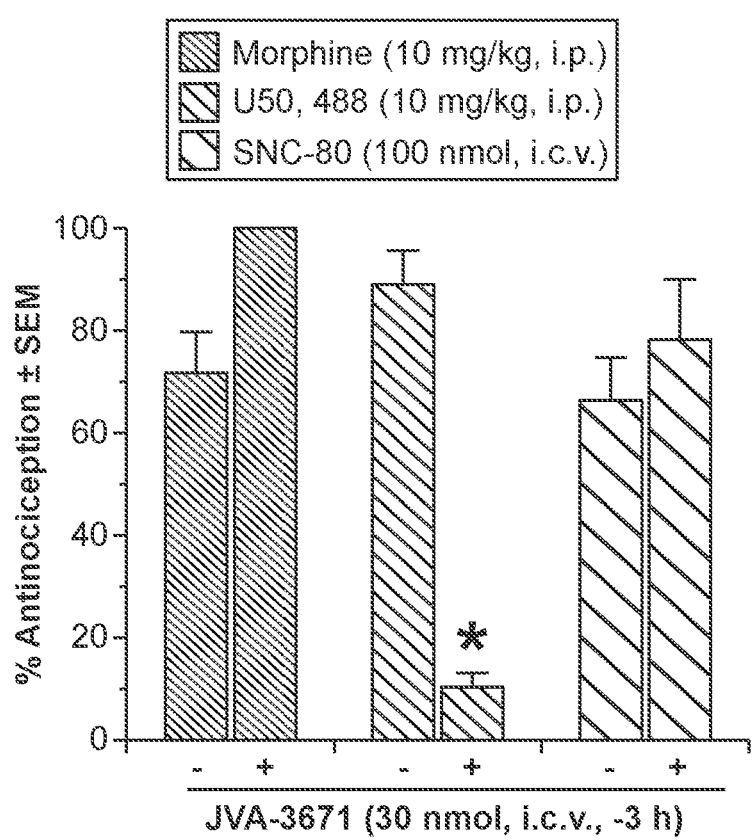

Following central (i.c.v.) administration, [D-2'-Pal$^4$]CJ-15,208 (JVA-3671) exhibits antinociception (FIG. 14A) mediated by delta opioid receptors (DOR)(FIG. 14B) and also exhibits KOR antagonist activity (FIG. 14C).

REFERENCES

S. S. Kulkarni, N. C. Ross, J. P. McLaughlin, and J. V. Aldrich, "Synthesis of Cyclic Tetrapeptide CJ 15,208, A Novel Kappa Opioid Receptor Antagonist" in Peptides for Youth, E. Escher, W. D. Lubell, and S. Del Valle, Eds., American Peptide Society, Adv. Exp. Med. Biol. 2009, 611, 269-270.

R. E. Dolle, M. Michaut, B. Martinez-Teipel, P. R. Seida, C. W. Ajello, A. L. Muller, R. N. DeHaven, P. J. Carroll, "Nascent structure-activity relationship study of a diastereomeric series of kappa opioid receptor antagonists derived from CJ-15,208," Bioorg. Med. Chem. Lett., 2009, 19, 3647-3650.

N. C. Ross, S. S. Kulkarni, J. P. McLaughlin and J. V. Aldrich, "Synthesis of CJ-15,208, a novel κ-opioid receptor antagonist, Tetrahedron Lett. 2010, 51, 5020-5023.

N. C. Ross, K. J. Reilley, T. F. Murray, J. V. Aldrich, and J. P. McLaughlin, Novel opioid cyclic tetrapeptides: Trp isomers of CJ-15,208 exhibit distinct opioid receptor agonism and short-acting kappa opioid receptor antagonism, Br. J. Pharmacol. 2012, 165, 1097-1108.

S. O. Eans, M. L. Ganno, K. J. Reilley, K. A. Patkar, S. N. Senadheera, J. V. Aldrich and J. P. McLaughlin, "The macrocyclic tetrapeptide [D-Trp]CJ-15,208 produces short acting κ opioid receptor antagonism in the CNS after oral administration," Br. J. Pharmacol. 2013, 169, 426-436.

J. V. Aldrich, S. N. Senadheera, N. C. Ross, K. A. Reilley, M. L. Ganno, S. E. Eans, T. F. Murray, and J. P. McLaughlin, "Alanine Analogs of [D-Trp]CJ-15,208: Novel Opioid Activity Profiles and Prevention of Drug- and Stress-Induced Reinstatement of Cocaine-Seeking Behavior," Br. J. Pharmacol. 2014, 171, 3212-3222.

J. V. Aldrich, N. Ross and S. Kulkarni, "Cyclic Tetrapeptides," U.S. Pat. No. 8,809,278.

J. V. Aldrich, and S. Senadheera, "Cyclic Tetrapeptide Stereoisomers," International Application No. PCT/US2015/040184, published as WO 2016/007956.

J. Y. Xie, M. De Felice, C. M. Kopruszinski, N. Eyde, J. LaVigne, B. Remeniuk, P. Hernandez, X. Yue, N. Goshima, M. Ossipov, T. King, J. M. Streicher, E. Navratilova, D. Dodick, H. Rosen, E. Roberts, and F. Porreca, "Kappa opioid receptor antagonists: A possible new class of therapeuticsfor migraine prevention," Cephalagia 2017, 37, 780-794.

M. Guerrero, M. Urbano, E.-K. Kim, A. M. Gamo, S. Riley, L. Abgaryan, N. Leaf, L. J. Van Orden, S. J. Brown, J. Y. Xie, F. Porreca, M. D. Cameron, H. Rosen, and E. Roberts, "Design and Synthesis of a Novel and Selective Kappa Opioid Receptor (KOR) Antagonist (BTRX-335140),"J. Med. Chem. 2019, 62, 1761-1780.

N. D. Buezo, D. L. McKinzie, C. H. Mitch, and C. Pedregal-Tercero, "Kappa Selective Opiod Receptor Antagonist," U.S. Pat. No. 8,173,695.

E. Roberts, M. A. Guerrero, M. Urbano, H. Rosen, R. M. Jones, C. M. Laxamana, X. Zhao, and E. D. Turtle, "Kappa Opioid Receptor Antagonists And Products And Methods Related Thereto," U.S. Patent Publ. No. 2019/0023700.

While certain embodiments have been illustrated and described, a person with ordinary skill in the art, after reading the foregoing specification, can effect changes, substitutions of equivalents and other types of alterations to the compounds of the present technology or salts, pharmaceutical compositions, tautomers, and/or enantioenriched mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

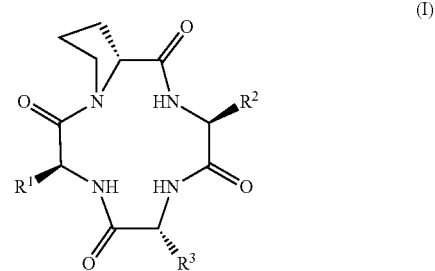

(I)

or a pharmaceutically acceptable salt and/or solvate thereof, wherein $R^1$ and $R^2$ are each independently

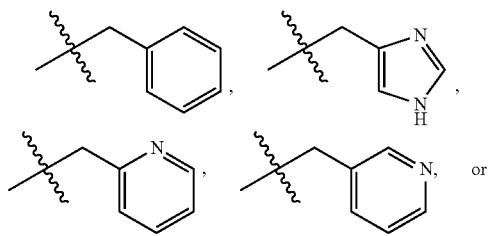

-continued

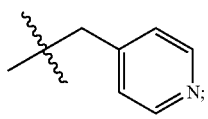

and

R³ is

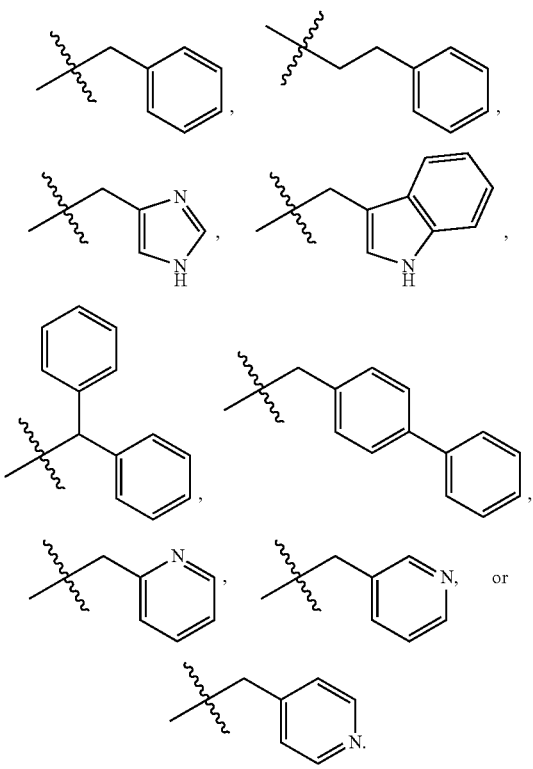

B. The compound of Paragraph A, wherein the compound is of Formula II

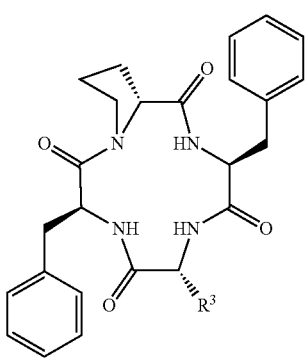

or a pharmaceutically acceptable salt and/or solvate thereof.

C. The compound of Paragraph A, wherein the compound is of Formula III

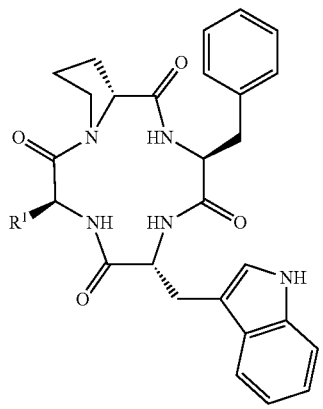

or a pharmaceutically acceptable salt and/or solvate thereof.

D. The compound of Paragraph A, wherein the compound is of Formula IV

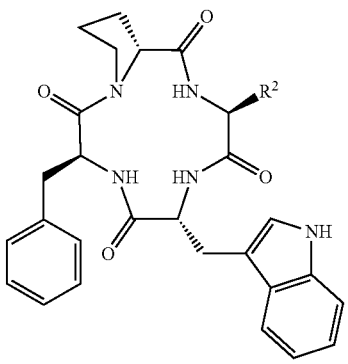

or a pharmaceutically acceptable salt and/or solvate thereof.

E. A composition comprising a compound of any one of Paragraphs A-D and a pharmaceutically acceptable carrier.

F. A pharmaceutical composition comprising an effective amount of a compound of any one of Paragraphs A-D and a pharmaceutically acceptable carrier, wherein the effective amount is effective for treating and/or inhibiting a CNS-related disorder in a subject.

G. The pharmaceutical composition of Paragraph F, wherein the effective amount is effective for treating and/or inhibiting pain, schizophrenia, schizoaffective disorder, migraine, depression, drug addiction, drug use, and/or drug seeking behavior in the subject.

H. The pharmaceutical composition of Paragraph F or Paragraph G, wherein the pharmaceutical composition is formulated for parenteral administration, intravenous administration, subcutaneous administration, and/or oral administration.

I. A method comprising administering an effective amount of a compound of any one of Paragraphs A-D or administering a pharmaceutical composition of any one of Paragraphs F-H to a subject suffering from a CNS-related disorder.

J. The method of Paragraph I, wherein the subject is suffering from pain, schizophrenia, schizoaffective disorder, migraine, depression, drug addiction, drug use, and/or drug seeking behavior.

K. The method of Paragraph I or Paragraph J, wherein administering comprises parenteral, intravenous, subcutaneous, or oral administration.

L. A method comprising administering an effective amount of a compound of any one of Paragraphs A-D to a subject suffering from pain, provided that the compound is not JVA-3627 or JVA-3629.

M. The method of Paragraph L, wherein administering comprises parenteral, intravenous, subcutaneous, or oral administration.

N. A method comprising contacting a kappa opioid receptor with a compound of any one of Paragraphs A-D wherein the contacting agonizes and/or antagonizes the kappa opioid receptor.

O. The method of Paragraph N, wherein the contacting occurs in vitro or in vivo.

P. The method of Paragraph N or Paragraph O, wherein the method further comprises contacting a mu opioid receptor, wherein the contacting does not antagonize the mu opioid receptor (such as by use of an amount effective to antagonize the kappa opioid receptor but not the mu opioid receptor).

Q. The method of any one of Paragraphs N-P, wherein the method further comprises contacting a delta opioid receptor, wherein the contacting does not antagonize the delta opioid receptor (such as by use of an amount effective to antagonize the kappa opioid receptor but not the delta opioid receptor).

Other embodiments are set forth in the following claims, along with the full scope of equivalents to which such claims are entitled.

What is claimed is:

1. A compound that is

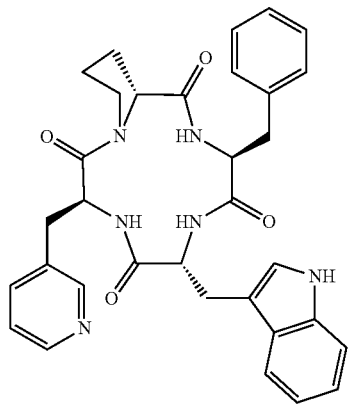

or a pharmaceutically acceptable salt and/or solvate thereof.

2. A composition comprising a compound of claim 1 and a pharmaceutically acceptable carrier.

3. A pharmaceutical composition comprising an effective amount of a compound of claim 1 and a pharmaceutically acceptable carrier, wherein the effective amount is effective for treating and/or inhibiting a CNS-related disorder in a subject.

4. The pharmaceutical composition of claim 3, wherein the effective amount is effective for treating and/or inhibiting schizophrenia, schizoaffective disorder, migraine, depression, drug addiction, drug use, and/or drug seeking behavior in the subject.

5. The pharmaceutical composition of claim 3, wherein the pharmaceutical composition is formulated for parenteral administration, intravenous administration, subcutaneous administration, and/or oral administration.

6. A method comprising administering a pharmaceutical composition of claim 3 to a subject suffering from a CNS-related disorder.

7. The method of claim 6, wherein the subject is suffering from schizophrenia, schizoaffective disorder, migraine, depression, drug addiction, drug use, and/or drug seeking behavior.

8. The method of claim 6, wherein administering comprises oral administration.

9. A method comprising administering an effective amount of a pharmaceutical composition of claim 3 to a subject suffering from pain.

10. The method of claim 9, wherein administering comprises oral administration.

11. A method comprising contacting a kappa opioid receptor with a pharmaceutical composition of claim 3 wherein the contacting agonizes and/or antagonizes the kappa opioid receptor.

12. The method of claim 11, wherein the contacting occurs in vivo.

13. The method of claim 11, wherein the contacting occurs in vitro.

14. The method of claim 11, wherein the method further comprises contacting a mu opioid receptor, wherein the contacting does not antagonize the mu opioid receptor.

15. The method of claim 11, wherein the method further comprises contacting a delta opioid receptor, wherein the contacting does not antagonize the delta opioid receptor.

16. The method of claim 13, wherein the method further comprises contacting a mu opioid receptor, wherein the contacting does not antagonize the mu opioid receptor.

17. The method of claim 13, wherein the method further comprises contacting a delta opioid receptor, wherein the contacting does not antagonize the delta opioid receptor.

* * * * *